(12) United States Patent
Lacey et al.

(10) Patent No.: US 11,732,227 B2
(45) Date of Patent: Aug. 22, 2023

(54) CELL CULTURE VESSELS WITH STABILIZER DEVICES

(71) Applicant: CORNING INCORPORATED, Corning, NY (US)

(72) Inventors: William Joseph Lacey, North Andover, MA (US); Gregory Roger Martin, Acton, ME (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 688 days.

(21) Appl. No.: 16/629,656

(22) PCT Filed: Jul. 13, 2018

(86) PCT No.: PCT/US2018/041974
§ 371 (c)(1),
(2) Date: Jan. 9, 2020

(87) PCT Pub. No.: WO2020/013845
PCT Pub. Date: Jan. 16, 2020

(65) Prior Publication Data
US 2021/0230528 A1    Jul. 29, 2021

(51) Int. Cl.
C12M 1/24    (2006.01)
C12M 1/00    (2006.01)
C12M 1/12    (2006.01)

(52) U.S. Cl.
CPC ............ *C12M 23/08* (2013.01); *C12M 23/34* (2013.01); *C12M 25/00* (2013.01)

(58) Field of Classification Search
None
See application file for complete search history.

(56) References Cited

U.S. PATENT DOCUMENTS 2,947,116 A    8/1960 Earle et al.
3,630,849 A    12/1971 Land et al.
(Continued)

FOREIGN PATENT DOCUMENTS

AU    2004256209 A1    1/2005
CA    2558946 A1    1/2005
(Continued)

OTHER PUBLICATIONS

Moon et al, "Optimizing Human Embryonic Stem Cells Differentiation Efficiency By Screening Size-Tunable Homogenous Embryoid Bodies"; Biomaterials; 35 (2014) 5987-5997.
(Continued)

*Primary Examiner* — William H. Beisner
(74) *Attorney, Agent, or Firm* — Chandra J. Duncan

(57) ABSTRACT

A cell culture vessel includes a vessel body, support columns, and a stabilizer device. The vessel body defines a cell culture chamber enclosed between a bottom wall and a top wall. The support column is within the cell culture chamber and extends between the top wall and the bottom wall. The stabilizer device covers a width and length of the cell culture chamber and has a column engaging structure that is sized to slidingly engage the support column such that the stabilizer device is movable along the support column as a liquid culture medium is received in the cell culture chamber. The support column guides the stabilizer device along a length of the support column as the stabilizer device rises with rising liquid level in the cell culture chamber during a liquid culture medium filling operation.

29 Claims, 9 Drawing Sheets

(56) References Cited

U.S. PATENT DOCUMENTS

| | | |
|---|---|---|
| 4,382,685 A | 5/1983 | Pearson |
| 4,498,785 A * | 2/1985 | de Bruyne ............. C12M 23/56 366/274 |
| 4,534,656 A * | 8/1985 | de Bruyne .......... B01F 33/4534 366/273 |
| 4,670,396 A | 6/1987 | Bear et al. |
| 4,760,028 A * | 7/1988 | deBruyne ........... B01F 33/4534 261/120 |
| 4,927,764 A | 5/1990 | Lyman et al. |
| 4,980,293 A | 12/1990 | Jeffs |
| 5,047,347 A | 9/1991 | Cline |
| 5,151,366 A | 9/1992 | Serkes et al. |
| 5,171,994 A | 12/1992 | Bahraman |
| 5,171,995 A | 12/1992 | Gast et al. |
| 5,240,854 A | 8/1993 | Berry et al. |
| 5,272,084 A | 12/1993 | O'Connell et al. |
| 5,319,436 A | 6/1994 | Manns et al. |
| 5,374,557 A | 12/1994 | Verma |
| 5,398,837 A | 3/1995 | Degrassi |
| 5,487,872 A | 1/1996 | Hafeman et al. |
| 5,554,536 A | 9/1996 | Rising |
| 5,598,262 A | 1/1997 | Jutard et al. |
| 5,665,562 A | 9/1997 | Cook |
| 5,693,537 A | 12/1997 | Wilson et al. |
| 5,707,869 A | 1/1998 | Wolf et al. |
| 5,710,043 A | 1/1998 | Pay |
| 5,736,397 A | 4/1998 | Garcia et al. |
| 5,759,494 A | 6/1998 | Szlosek |
| 5,766,949 A | 6/1998 | Liau et al. |
| 5,772,905 A | 6/1998 | Chou |
| 5,783,440 A | 7/1998 | Stevens |
| 5,792,653 A | 8/1998 | Weibezahn et al. |
| 5,858,309 A | 1/1999 | Mathus et al. |
| 5,972,694 A | 10/1999 | Mathus |
| 6,030,829 A | 2/2000 | Dannoux et al. |
| 6,039,972 A | 3/2000 | Barlow et al. |
| 6,306,646 B1 | 10/2001 | Saad et al. |
| 6,348,999 B1 | 2/2002 | Summersgill et al. |
| 6,514,464 B1 | 2/2003 | Knebel |
| 6,521,451 B2 | 2/2003 | Potter |
| 6,567,675 B1 | 5/2003 | Rosen et al. |
| 6,767,607 B2 | 7/2004 | Tanner et al. |
| 6,811,752 B2 | 11/2004 | Barbera-Guillem |
| 6,908,767 B2 | 6/2005 | Bader |
| 6,987,019 B1 | 1/2006 | Rogalsky |
| 7,470,424 B2 | 12/2008 | Kataoka et al. |
| 7,547,547 B2 | 6/2009 | Dang et al. |
| 7,674,346 B2 | 3/2010 | Clements et al. |
| 7,687,262 B2 | 3/2010 | Cattadoris |
| 7,691,369 B2 | 4/2010 | Kataoka et al. |
| 7,727,759 B2 | 6/2010 | Ozawa et al. |
| 7,745,209 B2 | 6/2010 | Martin et al. |
| 7,745,210 B2 | 6/2010 | Martin |
| 7,897,379 B2 | 3/2011 | Kenney et al. |
| 7,919,319 B2 | 4/2011 | Jervis et al. |
| 8,053,230 B2 | 11/2011 | Whittlinger |
| 8,143,053 B2 | 3/2012 | Yerbic |
| 8,148,152 B2 | 4/2012 | Kolossov et al. |
| 8,158,426 B2 | 4/2012 | Wilson et al. |
| 8,158,427 B2 | 4/2012 | Wilson et al. |
| 8,163,537 B2 | 4/2012 | Martin et al. |
| 8,168,432 B2 | 5/2012 | Wilson et al. |
| 8,178,345 B2 | 5/2012 | Bennett et al. |
| 8,273,572 B2 | 9/2012 | Martin et al. |
| 8,318,479 B2 | 11/2012 | Domansky et al. |
| 8,415,144 B2 | 4/2013 | Wilson et al. |
| 8,470,589 B2 | 6/2013 | Martin et al. |
| D685,497 S | 7/2013 | Kenney et al. |
| 8,486,692 B2 | 7/2013 | Simon |
| 8,597,597 B2 | 12/2013 | Deutsch et al. |
| 8,617,879 B2 | 12/2013 | Yu et al. |
| 8,697,443 B2 | 4/2014 | Wilson et al. |
| 8,759,017 B2 | 6/2014 | Owen et al. |
| 8,778,669 B2 | 7/2014 | Lacey et al. |
| 8,846,399 B2 | 9/2014 | Martin et al. |
| 8,906,685 B2 | 12/2014 | Takayama et al. |
| 8,932,544 B2 | 1/2015 | Mueller et al. |
| 9,039,883 B2 | 5/2015 | Guerrieri et al. |
| 9,040,293 B2 | 5/2015 | Gulzow et al. |
| 9,045,721 B2 | 6/2015 | Martin et al. |
| 9,068,281 B2 | 6/2015 | Wu et al. |
| 9,126,199 B2 | 9/2015 | Moritz et al. |
| 9,169,460 B2 | 10/2015 | Cecchi |
| D748,812 S | 2/2016 | Kenney et al. |
| 9,260,684 B1 | 2/2016 | Egeler et al. |
| 9,260,695 B2 | 2/2016 | Crowley et al. |
| 9,493,733 B2 | 11/2016 | Giles |
| 9,494,577 B2 | 11/2016 | McGarr et al. |
| 9,573,128 B1 | 2/2017 | McClelland |
| 9,587,213 B2 | 3/2017 | Morgan et al. |
| 9,732,317 B2 | 8/2017 | Wilson |
| 9,790,465 B2 | 10/2017 | Bennett et al. |
| 9,845,451 B2 | 12/2017 | Martin et al. |
| 9,862,918 B2 | 1/2018 | Ito |
| 10,254,274 B2 | 4/2019 | Miklas et al. |
| 11,441,121 B2 | 9/2022 | Bennett et al. |
| 2002/0022219 A1 | 2/2002 | Clements et al. |
| 2002/0172621 A1 | 11/2002 | Barbera-Guillem |
| 2003/0031829 A1 | 2/2003 | Tanner et al. |
| 2003/0104494 A1 | 6/2003 | Ravkin et al. |
| 2003/0183958 A1 | 10/2003 | Goff et al. |
| 2003/0186217 A1 | 10/2003 | Bader |
| 2003/0215941 A1 | 11/2003 | Campbell et al. |
| 2004/0091397 A1 | 5/2004 | Picard |
| 2004/0101955 A1 | 5/2004 | Whitley |
| 2004/0125266 A1 | 7/2004 | Miyauchi et al. |
| 2004/0216835 A1 | 11/2004 | Tanner et al. |
| 2004/0259242 A1 | 12/2004 | Malinge et al. |
| 2004/0259423 A1 | 12/2004 | Elbaz et al. |
| 2005/0032208 A1 | 2/2005 | Oh et al. |
| 2005/0047971 A1 | 3/2005 | Clements et al. |
| 2005/0074873 A1 | 4/2005 | Shanler et al. |
| 2005/0112030 A1 | 5/2005 | Gaus |
| 2005/0116717 A1 | 6/2005 | Dransfield et al. |
| 2005/0147959 A1 | 7/2005 | Frondoza et al. |
| 2006/0110822 A1 | 5/2006 | Robbins et al. |
| 2006/0234370 A1 | 10/2006 | Korpinen et al. |
| 2006/0252044 A1 | 11/2006 | Okumura et al. |
| 2006/0292654 A1 | 12/2006 | Reardon |
| 2007/0178441 A1 | 8/2007 | Li |
| 2007/0216897 A1 | 9/2007 | Sonda |
| 2008/0003671 A1 | 1/2008 | Martin |
| 2008/0009027 A1 | 1/2008 | Fraker et al. |
| 2008/0118974 A1 | 5/2008 | Martin et al. |
| 2008/0206857 A1 | 8/2008 | Kenney et al. |
| 2008/0268515 A1 | 10/2008 | Cullimore et al. |
| 2008/0297784 A1 | 12/2008 | Leblanc et al. |
| 2008/0299649 A1 | 12/2008 | Martin et al. |
| 2008/0300278 A1 | 12/2008 | Torrens Jover et al. |
| 2009/0017540 A1 | 1/2009 | Nishio et al. |
| 2009/0018033 A1 | 1/2009 | Morgan et al. |
| 2009/0029462 A1 | 1/2009 | Beardsley et al. |
| 2009/0037293 A1 | 2/2009 | Unger et al. |
| 2009/0170190 A1 | 7/2009 | Nishi et al. |
| 2009/0191620 A1 | 7/2009 | Martin et al. |
| 2009/0288963 A1 | 11/2009 | Guerrieri et al. |
| 2009/0298164 A1 | 12/2009 | Cattadoris et al. |
| 2009/0298166 A1 | 12/2009 | Fang et al. |
| 2010/0055774 A1 | 3/2010 | Wilson |
| 2010/0068793 A1 | 3/2010 | Ungrin et al. |
| 2010/0093075 A1 | 4/2010 | Muller |
| 2010/0112014 A1 | 5/2010 | Gilbert et al. |
| 2010/0112684 A1 | 5/2010 | Lee et al. |
| 2010/0119418 A1 | 5/2010 | Clements et al. |
| 2010/0170790 A1 | 7/2010 | Takahashi et al. |
| 2010/0190197 A1 | 7/2010 | Martin et al. |
| 2010/0197013 A1 | 8/2010 | Kamp et al. |
| 2010/0247386 A1 | 9/2010 | Deutsch et al. |
| 2010/0273258 A1 | 10/2010 | Lannutti et al. |
| 2010/0297600 A1 | 11/2010 | Cecchi |
| 2011/0086375 A1 | 4/2011 | Ungrin et al. |
| 2011/0097790 A1 | 4/2011 | Yerbic |
| 2011/0129923 A1 | 6/2011 | Wilson et al. |
| 2011/0229961 A1 | 9/2011 | Higashi et al. |

(56) References Cited

U.S. PATENT DOCUMENTS

| | | | |
|---|---|---|---|
| 2012/0064627 A1 | 3/2012 | Khine et al. |
| 2012/0129208 A1 | 5/2012 | Khine et al. |
| 2012/0129257 A1 | 5/2012 | Yu et al. |
| 2012/0219572 A1 | 8/2012 | Prockop et al. |
| 2013/0052331 A1 | 2/2013 | Kram et al. |
| 2013/0122539 A1 | 5/2013 | Li et al. |
| 2013/0122580 A1 | 5/2013 | Tsukada et al. |
| 2013/0143254 A1 | 6/2013 | Thomas et al. |
| 2013/0164848 A1 | 6/2013 | Naka et al. |
| 2013/0203159 A1 | 8/2013 | Itoh et al. |
| 2013/0344598 A1 | 12/2013 | Nistor |
| 2014/0004086 A1 | 1/2014 | Peak |
| 2014/0027784 A1 | 1/2014 | Wada et al. |
| 2014/0099717 A1 | 4/2014 | Fraker et al. |
| 2014/0106394 A1 | 4/2014 | Ko et al. |
| 2014/0106452 A1 | 4/2014 | Vukasinovic |
| 2014/0120573 A1 | 5/2014 | Tavana et al. |
| 2014/0178992 A1 | 6/2014 | Nakashima et al. |
| 2014/0221225 A1 | 8/2014 | Danen et al. |
| 2014/0226004 A1 | 8/2014 | Son et al. |
| 2014/0227784 A1 | 8/2014 | Ejiri et al. |
| 2014/0315296 A1 | 10/2014 | Wilson |
| 2014/0322806 A1 | 10/2014 | Bennett et al. |
| 2015/0004686 A1 | 1/2015 | Goral et al. |
| 2015/0064738 A1 | 3/2015 | Fsukada et al. |
| 2015/0072405 A1 | 3/2015 | Ito |
| 2015/0184119 A1 | 7/2015 | Fsukada et al. |
| 2015/0247112 A1 | 9/2015 | Orr et al. |
| 2016/0003796 A1 | 1/2016 | Kranbuehl |
| 2016/0017267 A1 | 1/2016 | Hansen et al. |
| 2016/0040120 A1 | 2/2016 | Gottwald et al. |
| 2016/0137962 A1 | 5/2016 | Ejiri et al. |
| 2016/0194588 A1 | 7/2016 | Guenat et al. |
| 2016/0216250 A1 | 7/2016 | Ritter et al. |
| 2017/0067019 A1 | 3/2017 | Ho |
| 2017/0073625 A1 | 3/2017 | Kasuto et al. |
| 2017/0226455 A1 | 8/2017 | Fang et al. |
| 2017/0267959 A1 | 9/2017 | Martin et al. |
| 2017/0283757 A1 | 10/2017 | Carter et al. |
| 2017/0306281 A1 | 10/2017 | Martin et al. |
| 2017/0342363 A1 | 11/2017 | Fang et al. |
| 2018/0166743 A1 | 6/2018 | Lee et al. |
| 2018/0201888 A1 | 7/2018 | Miwa et al. |
| 2018/0301754 A1 | 10/2018 | Badding et al. |
| 2019/0006707 A1 | 1/2019 | Sakamoto et al. |
| 2020/0239854 A1 | 7/2020 | Ayano et al. |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1168921 A | 12/1997 |
| CN | 1234112 A | 11/1999 |
| CN | 1867663 A | 11/2006 |
| CN | 1875093 A | 12/2006 |
| CN | 201261785 Y | 6/2009 |
| CN | 201626959 U | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 102687023 A | 9/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| CN | 107208025 A | 9/2017 |
| CN | 107460125 A * | 12/2017 |
| DE | 8309876 U1 | 12/1983 |
| DE | 10019862 A1 | 11/2001 |
| DE | 202006017853 U1 | 2/2007 |
| DE | 102009005526 A1 | 7/2010 |
| DE | 102014214077 A1 | 1/2016 |
| DE | 102014017728 A1 | 6/2016 |
| EP | 307048 A2 | 3/1989 |
| EP | 0605527 A1 | 7/1994 |
| EP | 0681846 A2 | 11/1995 |
| EP | 0800571 A2 | 10/1997 |
| EP | 834552 A1 | 4/1998 |
| EP | 965633 A1 | 12/1999 |
| EP | 1181349 A1 | 2/2002 |
| EP | 1348533 A2 | 10/2003 |
| EP | 1445022 A2 | 8/2004 |
| EP | 1988152 A1 | 11/2008 |
| EP | 2032262 A2 | 3/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 | 10/2016 |
| EP | 3296018 A1 | 3/2018 |
| EP | 3351615 A1 | 7/2018 |
| EP | 3372666 A1 | 9/2018 |
| GB | 2147100 A | 5/1985 |
| JP | 03-139350 A | 6/1991 |
| JP | 06-038734 A | 2/1994 |
| JP | 06327462 A | 11/1994 |
| JP | 09173049 A | 7/1997 |
| JP | 09-234811 A | 9/1997 |
| JP | 10210866 A | 8/1998 |
| JP | 10210966 A | 8/1998 |
| JP | 2001-106749 A | 4/2001 |
| JP | 2003135056 A | 5/2003 |
| JP | 2003180335 A | 7/2003 |
| JP | 2004129558 A | 4/2004 |
| JP | 2004-535829 A | 12/2004 |
| JP | 2005-080660 A | 3/2005 |
| JP | 2006-121991 A | 5/2006 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009050194 A | 3/2009 |
| JP | 2009-183288 A | 8/2009 |
| JP | 2009-542230 A | 12/2009 |
| JP | 2010088347 A | 4/2010 |
| JP | 2010-104327 A | 5/2010 |
| JP | 2010-518879 A | 6/2010 |
| JP | 2010158214 A | 7/2010 |
| JP | 2011-509686 A | 3/2011 |
| JP | 2011-521642 A | 7/2011 |
| JP | 2011172533 A | 9/2011 |
| JP | 2011-528226 A | 11/2011 |
| JP | 2012249547 A | 12/2012 |
| JP | 2013055911 A | 3/2013 |
| JP | 2014132869 A | 7/2014 |
| JP | 2015012827 A | 1/2015 |
| JP | 2015-029431 A | 2/2015 |
| JP | 2015073520 A | 4/2015 |
| JP | 2016-002023 A | 1/2016 |
| JP | 5845185 B2 | 1/2016 |
| JP | 2016-093149 A | 5/2016 |
| JP | 2016-136920 A | 8/2016 |
| JP | 2016136921 A | 8/2016 |
| JP | 2017-532970 A | 11/2017 |
| JP | 2018-108032 A | 7/2018 |
| KR | 1020140113139 A | 9/2014 |
| KR | 10-2014-0125662 A | 10/2014 |
| KR | 10-2017-0008539 A | 1/2017 |
| WO | 1992007063 A2 | 4/1992 |
| WO | 93/07258 A1 | 4/1993 |
| WO | 96/21851 A2 | 7/1996 |

(56) References Cited

FOREIGN PATENT DOCUMENTS

| | | |
|---|---|---|
| WO | 9815355 A2 | 4/1998 |
| WO | 1998031466 A1 | 7/1998 |
| WO | 2001080997 A1 | 11/2001 |
| WO | 2001092462 A1 | 12/2001 |
| WO | 2004/044120 A2 | 5/2004 |
| WO | 2004/094060 A1 | 11/2004 |
| WO | 2005047464 A2 | 5/2005 |
| WO | 2006043267 A1 | 4/2006 |
| WO | 2007/015770 A1 | 2/2007 |
| WO | 2007097120 A1 | 8/2007 |
| WO | 2008/006104 A2 | 1/2008 |
| WO | 2008/008149 A2 | 1/2008 |
| WO | 2008/106771 A1 | 9/2008 |
| WO | 2008118500 A1 | 10/2008 |
| WO | 2008/140295 A1 | 11/2008 |
| WO | 2008/149039 A2 | 12/2008 |
| WO | 2008153783 A1 | 12/2008 |
| WO | 2009094125 A2 | 7/2009 |
| WO | 2009148509 A1 | 12/2009 |
| WO | 2009148512 A2 | 12/2009 |
| WO | 2010008566 A2 | 1/2010 |
| WO | 2010/042072 A1 | 4/2010 |
| WO | 2010/069589 A1 | 6/2010 |
| WO | 2012036011 A1 | 3/2012 |
| WO | 2012/077683 A1 | 6/2012 |
| WO | 2012170232 A1 | 12/2012 |
| WO | 2013042360 A1 | 3/2013 |
| WO | 2013/108293 A1 | 7/2013 |
| WO | 2013/116449 A1 | 8/2013 |
| WO | 2014/042162 A1 | 3/2014 |
| WO | 2014072432 A1 | 5/2014 |
| WO | 2014/140181 A1 | 9/2014 |
| WO | 2014156455 A1 | 10/2014 |
| WO | 2014165273 A1 | 10/2014 |
| WO | 2014171782 A1 | 10/2014 |
| WO | 2014/179196 A1 | 11/2014 |
| WO | 2014196204 A1 | 12/2014 |
| WO | 2015033507 A1 | 3/2015 |
| WO | 2015/061907 A1 | 5/2015 |
| WO | 2015/087369 A1 | 6/2015 |
| WO | 2016/020992 A1 | 2/2016 |
| WO | 2016064757 A1 | 4/2016 |
| WO | 2016069885 A1 | 5/2016 |
| WO | 2016069892 A1 | 5/2016 |
| WO | 2016069895 A1 | 5/2016 |
| WO | 2016069917 A1 | 5/2016 |
| WO | 2016069930 A1 | 5/2016 |
| WO | 2016/157322 A1 | 10/2016 |
| WO | 2017025584 A1 | 2/2017 |
| WO | 2017/047735 A1 | 3/2017 |
| WO | 2017/077163 A1 | 5/2017 |
| WO | 2017142410 A1 | 8/2017 |
| WO | 2018/068034 A1 | 4/2018 |
| WO | 2018200893 A1 | 11/2018 |
| WO | 2019014621 A1 | 1/2019 |
| WO | 2019014627 A1 | 1/2019 |
| WO | 2019014635 A1 | 1/2019 |
| WO | 2019014636 A1 | 1/2019 |
| WO | 2019178039 A1 | 9/2019 |

OTHER PUBLICATIONS

Urich et al, "Multicellular Self-Assembled Spheroidal Model of the Blood Brain Barrier" Scientific Reports, 3, 1500, 8 Pages.
Murphy et al, "3D Bioprinting of Tissues and Organs"; Nature Biotechnology, vol. 32, No. 8, Aug. 2014, pp. 773-785.
Nortis; "Bridging the Gap Between in Vitro and in Vivo Research"; 16 Pages; (2015); https://www. nortisbio.com/.
Mimetas the Organ-On-A-Chip Company; "Organ-On-A-Chip Models for Science and Pharma"; 4 Pages; (Downloaded Mar. 9, 2020); https://mimetas.com/.
Otsuka et al, "Two-dimensional multiarray formation of hepatocyte spheroids on a microfabricated PEG-brush surface." ChemBioChem 2004; 5:850-855.
Peshwa et al., "Mechanistics of formation and ultrastructural evaluation of hepatocyte spheroids." In Vitro Cell Dev Biol Anim 1996; 32:197-203.
Organovo, "Pioneering Bioprinted Tissues To Treat Disease"; 2 Pages; (Downloaded Mar. 9, 2020) http://organovo.com/.
Rezende et al, "Scalable Biofabrication of Tissue Spheroids for Organ Printing"; Sciverse Science Direct, Procedia CIRP 5, (2013) 276-281.
Sa et al, "Round-bottomed Honeycomb Microwells: Embryoid body shape correlates with stem cell fate" Journal of Developmental Biology and Tissue Engineering vol. 4(2), pp. 12-22, May 2012.
Sakai et al, "Large-scale preparation and function of porcine hepatocyte spheroids." Int J Artif Organs 1996; vol. 19, No. 5, pp. 294-301.
Sakai et al, "Detachably Assembled Microfluidic Device for Perfusion Culture and Post-Culture Analysis of Spheroid Array"; Biotechnol. J. 2014, 9, 971-979.
Sakai et al, "Technique for the Control of Spheroid Diameter Using Microfabricated Chips"; Sciencedirect, ACTA Biomaterialia 3 (2007) 1033-1040.
Sart et al, "Three-dimensional aggregates of mesenchymal stem cells: cellular mechanisms, biological properties and applications" Tissue engineering, 2013, Part B, vol. 00, No. 00, 1-16.
Satoh et al, "A Pneumatic Pressure-Driven Multi-Throughput Microfluidic Circulation Culture System" Lab Chip, 2016, 16, 2339-2348.
Seldon et al, "Evaluation of Encapsulated Liver Cell Spheroids in a Fluidised-Bed Bioartificial Liver for Treatment of Ischaemic Acute Liver Failure in Pigs in a Translational Setting"; Plos One, 2013, 8(12), e82312.
Takezawa et al, "Morphological and immuno-cytochemical characterization of a hetero-spheroid composed of fibroblasts and hepatocytes" J Cell Sci 1992; 101:495-501.
Tara; "Innovating Predictive Cardiac Physiology"; 4 Pages; (2019) http://tarabiosystems.com/.
The Lab Depot® Products for Discovery Lab Supplies; Shake Flasks, 3 and 4 Baffles Product Information; 5 Pages (2019).
Tobe et al, "Receptor-mediated formation of multilayer aggregates of primary cultured adult rat hepatocytes on actose-substituted polystyrene" Biochem Biophys Res Commun 1992; 184(1):225-230.
Tong et al, "Long-term culture of adult rat hepatocyte spheroids." Exp Cell Res 1992; 200:326-332.
Truckenmuller et al, Thermoforming of Film-Based Biomedical Microdevices, Adv. Mater. 2011, 23, pp. 1311-1329.
Tung et al, "High-throughput 3D spheroid culture and drug testing using 384 hanging drop array" Analyst, 2011, 136 (3), 473-478.
Uchida et al, "An Injectable Spheroid System With Genetic Modification for Cell Transplantation Therapy"; Biomaterials, 35 (2014) 2499-2506.
Vinci et al, Advances in establishment and analysis of three-dimensional tumor spheroid-based functional assays for target validation and drug evaluation, BMC Biology 2012, 10:29.
Weegman et al, "Nutrient Regulation By Continuous Feeding Removes Limitations On Cell Yield in the Large-Scale Expansion of Mammalian Cell Spheroids"; Plos One, 2013, vol. 8, ISSUE 10, e76611, 10 PAGES.
Wikipedia, "Antiroll Tanks"; 3 Pages; Page Last Edited May 23, 2019.
Wrighton et al, "Forces of Change: Mechanics Underlying Formation of Functional 3D Drgan Buds" Cell Stem Cell, May 7, 2015; 16(5): 453-454.
Xu et al, "Characterisation of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003;189:100-111.
Yamada et al, "Efficient induction of hepatocyte spheroids in a suspension culture using a water-soluble synthetic polymer as an artificial matrix." J Biochem 1998; 123:1017-1023.
AxoSIM, Nerve-On-A-Chip Mini-Brain About Team; 6 Pages; (Downloaded Mar. 9, 2020); http://axosim.com/.
Corning Life Sciences Product Portfolio; 5 Pages Saved Mar. 6, 2020.

(56) References Cited

OTHER PUBLICATIONS

Madoux et al, "Building Phenotypic 3D Spheroid Hts Assays To Identify Synthetic Lethal Small Molecule Inhibitors of KRAS"; The Scripps Research Institute Molecular Screening Center and Department of Cancer Biology, Scripps Florida, Jupiter, Florida, Department of Pathology, Jupiter Medical Center, Jupiter, Florida.
Stemcell Technologies, Reproducible and Uniform Embryoid Bodies Using AggreWell Plates, StemCell Technologies, Technical Manual Version 3.0.0, Mar. 2011, Catalog #29146, pp. 1-28.
Achilli et al, "Advances in the Formation, Use and Understanding of Multi-Cellular Spheroids", Expert Opin. Biol. Ther. (2012) 12(10):1347-1360.
Alepee et al, "State-Of-The-Art 3D Cultures (Organs-On-A-Chip) in Safety Testing and Pathophysiology"; Transatlantic Think Tank for Toxicology, T4 Workshop Report, ALTEX 31, 4/14, pp. 441-477, Retrieved From: http://dx.doi.org/10.14573/altex1406111 (Jul. 14, 2014).
Aline, "We Engineer Microfluidic Products"; 7 Pages; (2020) https://alineinc.com/.
G-Plate: Accelerate your cell cultures to the next dimension, "An original cell culture model allowing for island-shaped 3D cell aggregates", 1 page, retrieved Sep. 8, 2015.
Anada et al, "An Oxygen-Permeable Spheroid Culture System for the Prevention of Central Hypoxia and Necrosis of Spheroids"; Biomaterials 33 (2012) 8430-8441.
Bartosh et al, "Aggregation of Human Mesenchymal Stromal Cells (MSCS) Into 3D Spheroids Enhances Their Antiinflammatory Properties"; PNAS, Aug. 3, 2010, 107 (31):13724-13729.
BIOIVT Elevating Science ®; 6 Pages; (2020); http://www.hepregen.com/.
Carver et al, "Multicellular Tumor Spheroids as a Model for Assessing Delivery of Oligonucleotides in Three Dimensions"; Molecular Therapy-Nucleic Acids (2014) 3, E153; 8 Pages.
Chen et al, "Microfluidic array for three-dimensional perfusion culture of human mammary epithelial cells"; Biomedical Microdevices, 2011, 13(4):753-758.
Cheng et al, "MICRORNA-34a Targets Forkhead Box J2 To Modulate Differentiation of Endothelial Progenitor Cells in Response To Shear Stress", J Mol Cell Cardiol. 74 (2014) 4-12.
Choi et al, "Feasibility of a simple double-layered coculture system incorporating metabolic processes of the intestine and liver tissue: application to the analysis of benzo[a]pyrene toxicity", Toxicology in Vitro 18 (2004) 393-402.
CN-BIO, "Transforming Drug Discovery and the Lives of Patients"; 5 Pages; (2020) http://cn-bio.com/.
Colazzo et al, "Shear Stress and VEGF Enhance Endothelial Differentiation of Human Adipose-Derived Stem Cells", Growth Factors, 2014, 32(5):139-149.
Corning® HTS TRANSWELL® -96 Tissue Culture Systems, Permeable Supports for High Throughput Screening Applications; 2 PAGES (2004).
Tissue Dynamics, "Disruptive Drug Development"; 3 Pages; (Downloaded Mar. 9, 2020); https://www. tissuedynamics.com/.
Dolznig et al, "Organotypic spheroid cultures to study tumor-stroma interaction during cancer development", Drug Discovery Today: Disease Models, 2011, 8(2-3):113-118.
Domansky et al, "Perfused Multiwell Plate for 3D Liver Tissue Engineering", Lab Chip, 2010, 10:51-58.
Emulate, 6 Pages; (2019) https://emulatebio.com/.
Tissuse, "Emulating Human Biology, Pioneering Human-On-A-Chip Developments"; 1 Page; (Downloaded Mar. 9, 2020) https://www.tissuse.com/en/.
Endo et al, "Gene transfection to spheroid culture system on micropatterned culture plate by polyplex nanomicelle: a novel platform of genetically-modified cell transplantation". Drug Deliv. and Transl. Res., 2012, 2:398-405.
Engelberg et al, "Essential operating principles for tumor spheroid growth", BMC Systems Biology 2008, 2:110, 19 pages.

Friedrich et al, "Experimental anti-tumor therapy in 3-D: spheroids—old hat or new challenge?" Int J Radiat Biol 2007, 83(11-12):849-871.
Friedrich et al, "Spheroid-based drug screen: considerations and practical approach", Nature protocols, 2009, 4(3):309-323.
Frith et al, "Dynamic three-dimensional culture methods enhance mesenchymal stem cell properties and increase therapeutic potential", Tissue engineering, 2010, 16(4):735-749.
Fukuda et al, "Efficacy of a polyurethane foam/spheroid artificial liver by using human hepatoblastoma cell line (Hep G2)", Cell Transplantation, 2003, 12:51-58.
GeoCHEM Incorporated, Product Line; https://www.geocheminc.com, 4 Pages; (2020).
Haycock, "3D cell culture: a review of current approaches and techniques", Methods Mol Biol, 2011; 695:1-15.
Hirschhaeuser et al, "Multicellular tumor spheroids: An underestimated tool is catching up again", Journal of Biotechnology 148 (2010) 3-15.
Howes et al, "3-Dimensional Culture Systems for Anti-Cancer Compound Profiling and High-Throughput Screening Reveal Increases in EGFR Inhibitor-Mediated Cytotoxicity Compared to Monolayer Culture Systems"; Plos One; Sep. 2004, 9(9), 11 Pages.
Hribar et al, "Nonlinear 3D Projection Printing of Concave Hydrogel Microstructures for Long-Term Multicellular Spheroid and Embryoid Body Culture"; Lab Chip, 2015, 15, 2412-2418.
Hwang et al, "Microwell-Mediated Control of Embryoid Body Size Regulates Embryonic Stem Cell Fate Via Differential Expression of WNT5A and WNT11"; PNAS, 2009, 106(40):16978-16983.
HµREL ® Corporation, Bioanalytic Tools Company; 2 Pages; (2013); http://hurelcorp.com/.
Jeon et al, "Combined Effects of Flow-Induced Shear Stress and Micropatterned Surface Morphology on Neuronal Differentiation of Human Mesenchymal Stem Cells" J Biosci Bioeng, 2014, 117(2):242-247.
Jiang et al, "Shear Enhances Thrombopoiesis and Formation of Microparticles That Induce Megakaryocytic Differentiation of Stem Cells", Blood, Sep. 25, 2014; 124(13):2094-2103.
Kelm et al, "Method for generation of homogeneous multicellular tumor spheroids applicable to a wide variety of cell types", Biotechnology and Bioengineering 2003; 83(2):173-180.
Kim et al, "Shear Stress Induced by an Interstitial Level of Slow Flow Increases the Osteogenic Differentiation of Mesenchymal Stem Cells Through TAZ Activation" PLoS ONE, Mar. 21, 2014; 9(3), e92427, 9 pages.
Koide et al, "Formation of multicellular spheroids composed of adult rat hepatocytes in dishes with positively charged surfaces and under other nonadherent environments", Exp Cell Res 1990; 186:227-235.
Kunz-Schughart et al, "The use of 3-D cultures for high-throughput screening: the multicellular spheroid model", J Biomol Screen 2004, 9(4):273-285.
Kutsuzawa et al, "Highly Robust Protein Production by Co-Culture of CHO Spheroids Layered on Feeder Cells in Serum-Free Medium"; Colloid Polym Sci (2014) 292; 839-848.
Labusca, "Scaffold free 3D culture of mesenchymal stem cells; implications for regenerative medicine", J Transplant Stem Cel Biol 2015 2(1): 8.
Landry et al, "Spheroidal aggregate culture of rat liver cells: histotypic reorganization, biomatrix deposition, and maintenance of functional activities" J Cell Biol 1985; 101:914-923.
Lau et al, "Evaluation of a Novel in Vitro CACO-2 Hepatocyte Hybrid System for Predicting In Vivo Oral Bioavailability" Drug Metabolism and Disposition, vol. 32, No. 9, pp. 937-942, 2004.
Liquid Surge Control, LLC; "The Latest in Drop-In Baffle Technology"; 2 Pages; (2019).
Liu et al, "Quasi-spherical microwells on superhydrophobic substrates for long term culture of multicellular spheroids and high throughput assays" Biomaterials 35 (2014) pp. 6060-6068.
Liu et al, "Advanced Micromachining of Concave Microwells for Long Term On-Chip Culture of Multicellular Tumor Spheroids", ACS Appl. Mater. Interfaces, 2014, 6, 8090-8097.

(56) References Cited

OTHER PUBLICATIONS

Lu et al, "Galactosylated PVDF membrane promotes hepatocyte attachment and functional maintenance" Biomaterials 24 (2003) 4893-4903.

Markovitz-Bishitz, "A polymer microstructure array for the formation, culturing, and high throughput drug screening of breast cancer spheroids" Biomaterials 31 (2010) 8436 8444.

Messner et al, Multi-cell type human liver microtissues for hepatotoxicity testing. Archives of Toxicology, Nov. 11, 2012, 5 pages.

Elveflow; "Microfluidics Innovation Center"; 6 Pages; (Downloaded Mar. 9, 2020); https://www.elveflow.com/.

Mironov et al, "Organ Printing: Tissue Spheroids as Buliding Blocks" Biomaterials, 2009; 30 (12): 2164-2174.

International Search Report And Written Opinion Of The International Searching Authority; PCT/US2018/041974; dated Mar. 14, 2019; 10 Pages; European Patent Office.

Lovett et al. "Vascularization Strategies for Tissue Engineering" Tissue Engineering Part B, 2009, vol. 15, No. 3, pp. 353-370.

Office Action dated Aug. 8, 2019 pertaining to U.S. Appl. No. 15/708,473, filed Sep. 19, 2017, 20 pgs.

"Laboratory Flasks Selection Guide: Types, Features, Applications", Engineering360, <https://www.globalspec.com/learnmore/labware_scientific_instruments/labware_consumables/laboratory_flasks#:~:text=Laboratory%20flasks%20are%20lab%20vessels,the%20opening%20at%20the%20neck.> accessed Apr. 8, 2022 (Year: 2022).

Achilli et al., "Advances In The Formation, Use And Understanding Of Multi-cellular Spheroids", Expert Opinion On Biological Therapy, vol. 12, No. 10, Jul. 2012, pp. 1347-1360.

Brandrup et al., "Polymer Handbook", Fourth Edition, Wiley-Interscience Publication, , Permeability and diffusion data, 1999, 9 pages (Contributors; Preface).

Curcio et al. "Mass transfer and metabolic reactions in hepatocyte spheroids cultured in rotating wall gas-permeable membrane system." Biomaterials 28 (2007) 5487-5497. (Year: 2007).

Endo et al., "Gene transfection to spheroid culture system on micropatterned culture plate by polyplex nanomicelle: a novel platform of genetically-modified cell transplantation", Drug Deliv. and Transl. Res., 2012, vol. 2, p. 398-405.

Evenou et al. "Spontaneous Formation of Highly Functional Three-Dimensional Multilayer from Human Hepatoma Hep G2 Cells Cultured on an Oxygen-Permeable Polydimethylsiloxane Membrane." Tissue Engineering: Part C vol. 16, No. 2, 2010, pp. 311-318. (Year: 2010).

Hsiao et al., "Effects of 3D Microwell Culture on Initial Fate Specification in Human Embryonic Stem Cells", Published in final edited form as AIChE J. vol. 60 No.4, Apr. 2014, pp. 1225-1235.

Huang et al., "Preparation of dense Ta-LLZO/MgO composite Li-ion solid electrolyte: Sintering, microstructure, performance and the role of MgO", Journal of Energy Chemistry, vol. 39, 2019, pp. 8-16.

Junji Fukuda et al., "Hepatocyte Spheroid Arrays Inside Microwells Connected With Microchannels", Biomicrofluidics 5, 2011, pp. 10.

Koike et al. "Characterization of Embryo id Bodies of Mouse Embryonic Stem Cells Formed under Various Culture Conditions and Estimation of Differentiation Status of Such Bodies." Journal of Bioscience and Bioengineering vol. I 04, No. 4, 294-299. 2007. (Year: 2007).

Lin et al., "La2Zr2O7 and MgO co-doped composite Li-Garnet solid electrolyte", Journal of Energy Chemistry, vol. 40, 2020, pp. 132-136.

Lonza Inc., "SeaPrep Agarose: An Ultralow Gelling, Soft Agarose", Available Online at <http://www.lonzabio.jp/catalog/pdf/pd/PD031.pdf>, 2007, pp. 1-4.

Martin et al., "Agarose And Methylcellulose Hydrogel Blends For Nerve Regeneration Applications", J. Neural Eng., vol. 5, 2008, pp. 221-231.

McMillan, "Shear stress in microfluidic devices" Darwin Microfludics interner article (Year: 2017).

Polyimide: Japan Polyimide and Aromatic Polymers Study Group, 2010, pp. 364-371 Table 2.

WO 2017/077163 (Year: 2017).

WO-2008149039 translation (Year: 2008).

Yang et al.,"An Agarose-Gel Based Method for Transporting Cell Lines", Current Chemical Genomics, vol. 3, Jan. 2009, pp. 50-53.

Zuidema et al., "Fabrication And Characterization Of Tunable Polysaccharide Hydrogel Blends For Neural Repair", Acta Biomaterialia, vol. 7, No. 4, Apr. 2011, pp. 1634-1643.

Chinese Patent Application No. 201880051225.6, Office Action, dated Feb. 13, 2023, 4 pages Chinese Patent Office.

\* cited by examiner

CELL CULTURE VESSELS WITH STABILIZER DEVICES

This application claims the benefit of priority under 35 U.S.C. § 365 of International Patent Application Serial No. PCT/US2018/041974 filed on Jul. 13, 2018, the content of which is relied upon and incorporated herein by reference in its entirety.

BACKGROUND

Field

The present specification generally relates to cell culture vessels used for growing cells, more specifically, to cell culture vessels that include stabilizer devices that restrict liquid motion in the cell culture vessel.

Technical Background

Generally, three-dimensional (3D) cell cultures can be better suited for simulating an environment of natural tissues and organs than two-dimensional (2D) cell cultures. In 2D cell cultures, cells are grown on planar surfaces of a flat dish, typically made of a plastic material that is rigid. Accordingly, this creates an unnatural environment for the cells to be grown in as the cells attach to the planar surface of the plastic and spread uniformly along the flat dish. This can cause the cells cultured therein to form unnatural attachments to proteins.

In contrast, cells grown in 3D cell cultures are able to attach to other deposited cells within the three-dimensional environment thereby forming spheroids, creating a more natural interaction between the cells. This native arrangement of cells provides a flexible configuration, similar to that of natural tissues. Providing an accurate exemplification of a tissue microenvironment is desirable when conducting experimental research for developing therapies against diseases to increase accuracy. Since cells do not grow in 2D within a human body, it is desirable to develop these therapies in a 3D culture as that more closely resembles the environment in which the developed drug will ultimately be applied in.

A concern for using 3D cell cultures is the susceptibility of the spheroids formed therein to be damaged when transporting the vessel. Due to the presence of liquid and various volumes of open area within the vessel, transporting the vessel generally causes the liquid contained therein to move unintentionally which can cause turbulence within the vessel. Since the cells in a 3D cell culture are not attached to any surface of the vessel, unlike cells grown in 2D cell cultures, this turbulence may influence the cells out of the respective microcavities that they are being cultured in, thereby causing a loss of spheroidicity and the size of the spheroids to become heterogeneous.

Accordingly, a need exists for stabilizing liquid motion within 3D spheroid culture vessels.

SUMMARY

According to one embodiment, a cell culture vessel includes a vessel body that defines a cell culture chamber enclosed between a bottom wall and a top wall; a support column within the cell culture chamber extending between the top wall and the bottom wall; and a stabilizer device covering a width and length of the cell culture chamber having a column engaging structure that is sized to slidingly engage the support column such that the stabilizer device is movable along the support column as a liquid culture medium is received in the cell culture chamber. The support column guides the stabilizer device along a length of the support column as the stabilizer device rises with rising liquid level in the cell culture chamber during a liquid culture medium filling operation.

According to another embodiment, a cell culture vessel includes a vessel body that defines a cell culture chamber enclosed within a bottom wall, a top wall, and a pair of side walls. The bottom wall comprises a cell culture surface, wherein the vessel body is configured to receive a medium such that the medium is deposited along the culture surface. The cell culture vessel further includes a support column positioned within the cell culture chamber that extends between the top wall and the bottom wall; and a stabilizer device comprising a pair of outboard wings and a central wing disposed within the cell culture chamber. The central wing is disposed between the pair of outboard wings and the pair of outboard wings are pivotally coupled to the pair of side walls, the central wing including column engaging structure that is sized to slidingly engage the support column. The support column guides the central wing along a height of the support column as the central wing is raised.

According to another embodiment, a method of stabilizing a liquid medium within a cell culture vessel includes positioning a stabilizer device within a cell culture chamber within a vessel body of the cell culture vessel; and engaging a column engaging structure of the stabilizer device with a support column such that the stabilizer device is moveable along the support column between a top wall and a bottom wall of the vessel body as the cell culture chamber is filled with liquid cell culture medium.

Additional features and advantages of the cell culture vessels described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
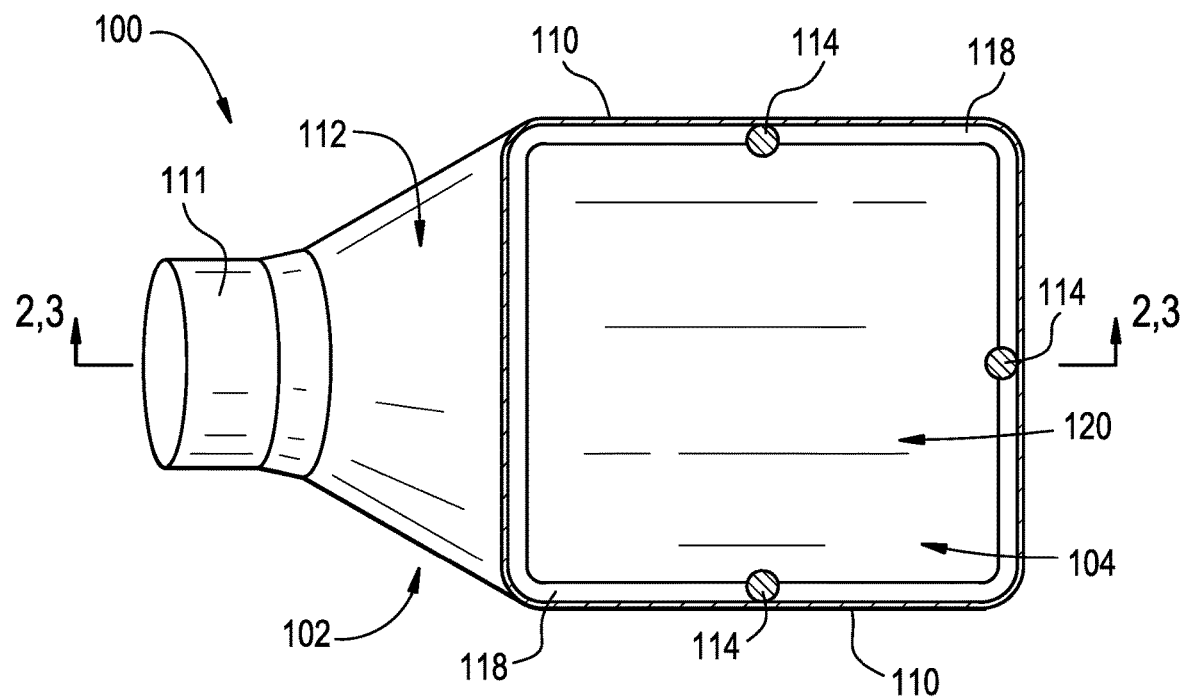
FIG. 1 depicts a top cross-sectional view of a cell culture vessel with a stabilizer device, the cell culture vessel including a microcavity substrate and support columns therein according to one or more embodiments shown and described herein.

Reference will now be made in detail to various embodiments of cell culture vessels with various stabilizer devices located therein, examples of which are illustrated in the accompanying drawings. Whenever possible, the same reference numerals will be used throughout the drawings to refer to the same or like parts. Directional terms as used herein—for example up, down, right, left, front, back, top, bottom, distal, and proximal—are made only with reference to the figures as drawn and are not intended to imply absolute orientation.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural referents unless the context clearly dictates otherwise. Thus, for example, reference to "a" component includes aspects having two or more such components, unless the context clearly indicates otherwise.

Figure 2:
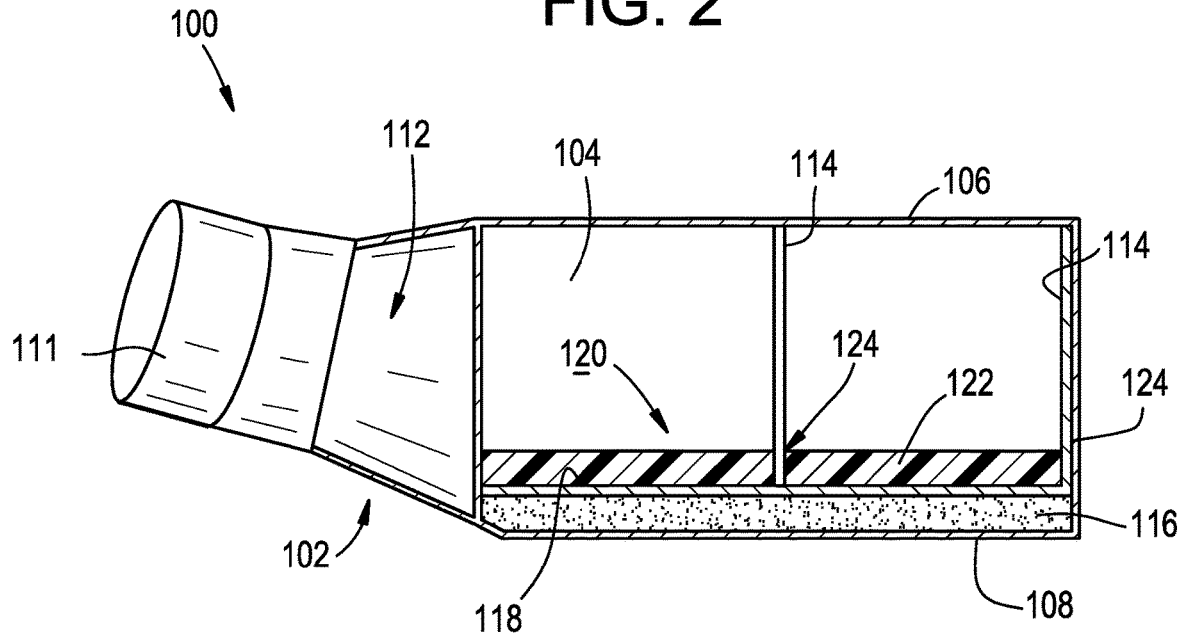
FIG. 2 depicts a side cross-sectional view of the cell culture vessel of FIG. 1 with a shelf positioned between the microcavity substrate and the stabilizer device, the cross-section taken along line 2-2 of FIG. 1.

Referring now to FIG. 1 and FIG. 2, one embodiment of a cell culture vessel 100 is shown. Cell culture vessel 100 has a vessel body 102 that defines a cell culture chamber 104 formed within vessel body 102. In particular, vessel body 102 of cell culture vessel 100 comprises atop wall 106, a bottom wall 108, and a plurality of sidewalls 110 extending between top wall 106 and bottom wall 108. Vessel body 102 further includes a side entry port 112 that is configured to provide fluid access into cell culture chamber 104. As will be described in greater detail below, cell culture vessel 100 is operable to receive a liquid medium into cell culture chamber 104 via side entry port 112. Cell culture vessel 100 further includes a plurality of support columns 114 extending within cell culture chamber 104. Support columns 114 extend between top and bottom walls 106, 108 such that support columns 114 are securely fixed at opposing ends to top and bottom walls 106, 108, respectively. In the present example, vessel body 102 includes three support columns 114 within cell culture chamber 104 extending along sidewalls 110. It should be understood that vessel body 102 of cell culture vessel 100 may include additional or fewer support columns 114. Additionally, support columns 114 may extend at varying positions and orientations relative to vessel body 102 than that shown.

As best seen in FIG. 2, cell culture vessel 100 includes a cell culture surface 116 positioned along bottom wall 108 of vessel body 102. Cell culture surface 116 is a substrate that includes a plurality of microcavities sized and shaped to receive at least one cell therein. Accordingly, cell culture surface 116 is a cell culturing area that is configured to facilitate the growth and development of the cells within cell culture chamber 104. Cell culture vessel 100 further includes a shelf 118 extending around an inner perimeter of cell culture chamber 104 such that shelf 118 is integrally attached to sidewalls 110. Shelf 118 is positioned over cell culture surface 116 and provides a vertical clearance between cell culture surface 116 and a remaining portion of cell culture chamber 104. As will be described in greater detail below, shelf 118 is sized and shaped to extend into cell culture chamber 104 to thereby inhibit features within cell culture chamber 104 from encountering cell culture surface 116. Although shelf 118 is included within cell culture chamber 104 in the present example, it should be understood that in some versions shelf 118 may be omitted entirely. Alternatively, it should be understood that cell culture vessel 100 may include additional shelves 118 and/or shelves 118 of varying shapes or sizes.

Cell culture vessel 100 further includes a stabilizer device 120 positioned within cell culture chamber 104. Stabilizer device 120 comprises a substrate 122 that is sized and shaped to fit within cell culture chamber 104 such that substrate 122 has a width and length that covers a corresponding width and length of cell culture chamber 104. In other words, stabilizer device 120 is sized to have a footprint that is at least 50 percent of cell culture surface 116 (i.e. the cell culturing area within cell culture chamber 104). Further, substrate 122 is sized in accordance with shelf 118 such that substrate 122 is configured to engage shelf 118 when in a lowered position. In this instance, shelf 118 is configured to inhibit substrate 122 from encountering cell culture surface 116 by providing an obstruction within cell culture chamber 104 between substrate 122 and cell culture surface 116.

In the present example, substrate 122 is formed of a low-density polymer that has a density no greater than about 1.0 g/cm$^3$ at room temperature such that substrate 122 is configured to have a lower density than a liquid culture medium 10. In some instances, liquid culture medium 10 may include water. Substrate 122 further includes a plurality of column-engaging structures 124 formed therethrough that are sized and shaped to slidingly engage the plurality of support columns 114 therein. Accordingly, substrate 122 includes a number of column-engaging structures 124 formed as slots in accordance with a number of support columns 114 included within cell culture vessel 100. In the present example, substrate 122 includes three column-engaging structures 124 that are sized, shaped, and positioned along substrate 122 to correspond with the size, shape, and fixed location of support columns 114 of cell culture vessel 100 within cell culture chamber 104. With substrate 122 fixed to vessel body 102 via the engagement between column-engaging structures 124 and support columns 114, substrate 122 is thereby restricted in movement within cell culture chamber 104. In particular, substrate 122 is operable to slidably translate within cell culture chamber 104 along a length of support columns 114. Further, substrate 122 is restricted from contacting cell culture surface 116 by the presence of shelf 118 positioned between substrate 122 and cell culture surface 116.

Figure 3:
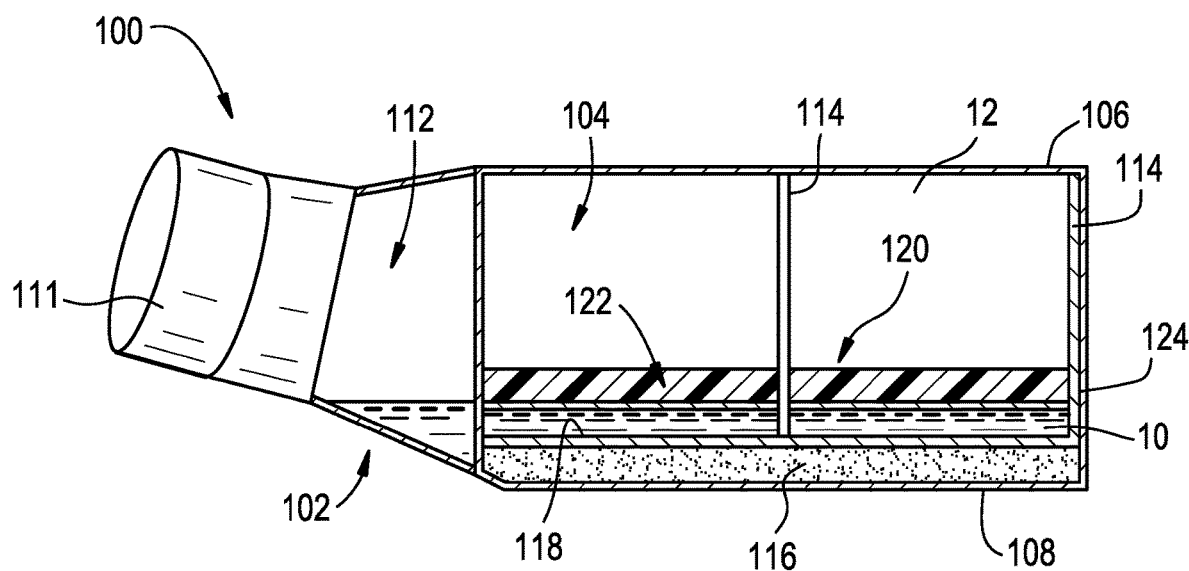
FIG. 3 depicts a side cross-sectional view of the cell culture vessel of FIG. 1 filled with a liquid medium and the stabilizer device floating along a surface of the liquid medium, the cross-section taken along line 3-3 of FIG. 1.

In use, a plurality of cells are deposited within cell culture vessel 100 such that cell culture chamber 104 is operable to house the cells within the plurality of microcavities of cell culture surface 116. With the plurality of cells received along the microcavity substrate of cell culture surface 116, the development of the cells is facilitated by exposing cell culture surface 116 to various fluids during a liquid culture medium filling operation. In particular, a liquid culture medium 10 is deposited within cell culture chamber 104 by opening a cap 111 of vessel body 102 to thereby facilitate access to side entry port 112. As seen in FIG. 3, liquid culture medium 10 is inserted into cell culture chamber 104 via side entry port 112 thereby transferring liquid culture medium 10 toward cell culture surface 116. As liquid culture medium 10 enters cell culture chamber 104, substrate 122 moves upward toward top wall 106 due to the lower density of substrate 122 relative to liquid culture medium 10. In other words, due to substrate 122 comprising a low density polymer, substrate 122 is operable to float over liquid culture medium 10 as liquid culture medium 10 is received within cell culture chamber 104. Substrate 122 is guided toward top wall 106 by support columns 114 such that substrate 122 continues to slidingly translate along a length of support columns 114 until cell culture vessel 100 ceases further receipt of liquid culture medium 10 within cell culture chamber 104.

In this instance, with substrate 122 positioned directly atop a surface of liquid culture medium 10, as seen in FIG. 3, stabilizer device 120 serves to stabilize movement of liquid culture medium 10 within cell culture chamber 104. In particular, any movement of cell culture vessel 100 with liquid culture medium 10 stored therein may normally cause liquid culture medium 10 to move within cell culture chamber 104 due to the presence of open volume areas 12 therein. However, with substrate 122 positioned against a top surface of liquid culture medium 10, stabilizing device 120 is configured to inhibit the fluidity and/or free motion of liquid culture medium 10 within cell culture chamber 104. Further stabilizing substrate 122 within cell culture chamber 104 is the engagement between support columns 114 and column-engaging structures 124. Accordingly, stabilizing device 120 of the present example is configured to preserve the condition of the cells received within the microcavities of the cell culture surface 116 by inhibiting movement of liquid control medium 10 and isolating liquid control medium 10 from open volume areas 12 within cell culture chamber 104.

Figure 4:
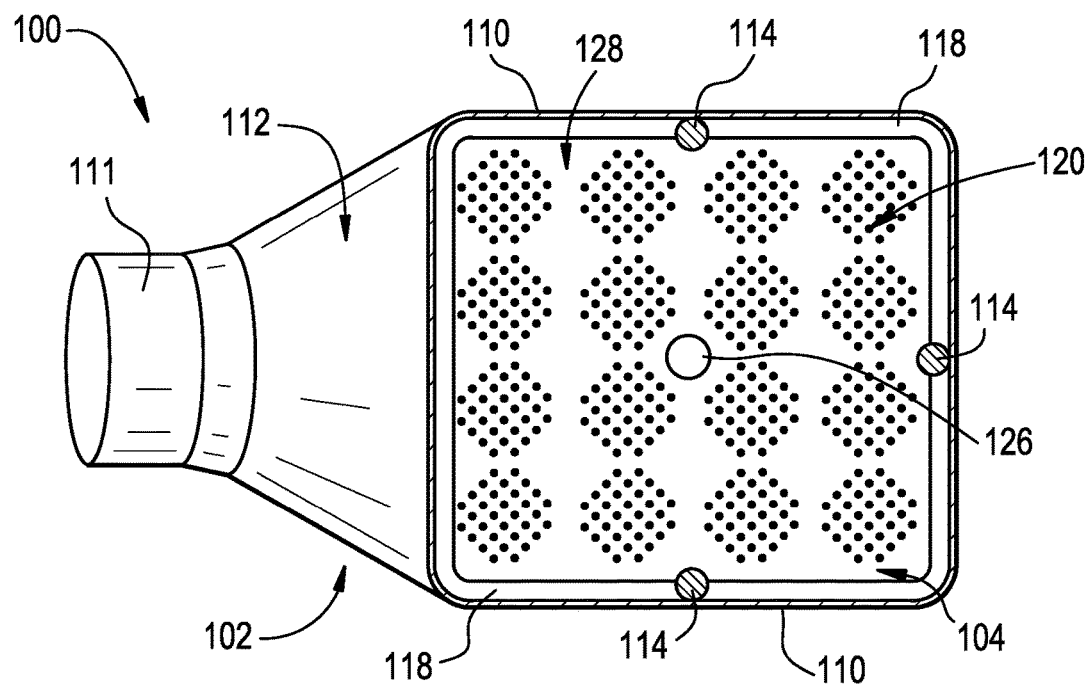
FIG. 4 depicts a top cross-sectional view of a cell culture vessel with a stabilizer device including a magnet formed therein according to one or more embodiments shown and described herein.

Additionally or alternatively, stabilizer device 120 may include a magnet 126 integrally formed therein, as seen in FIG. 4. In this instance, magnet 126 is unitarily integrated with substrate 122 and comprises a predetermined polarization. Magnet 126 is operable to influence movement of substrate 122 within cell culture chamber 104 and along the length of support columns 114 in response to the placement of an external magnet adjacent top wall 106 and/or bottom wall 108. The external magnet may comprise an opposite polarization as magnet 126 such that the external magnet and magnet 126 are magnetically attracted to one another. In another embodiment, the external magnet may comprise a same polarization as magnet 126 such that the magnets repel one another. Accordingly, positioning the external magnet adjacent to vessel body 102 along top wall 106 or bottom wall 108 will cause magnet 126 to interact with the external magnet and thereby move substrate 122 toward the respective wall 106, 108 that the external magnet is positioned adjacent to.

In use, stabilizer device 120 is raised within cell culture chamber 104 via either the liquid filling operation of liquid culture medium 10 within cell culture chamber 104 as described above, and/or by positioning the external magnet against top wall 106 of vessel body 102. In each instance, substrate 122 is lifted relative to cell culture surface 116 such that liquid culture medium 10 is deposited directly over cell culture surface 116 without interference by substrate 122. At the conclusion of the liquid filling operation, substrate 122 is rested over liquid culture medium 10 such that substrate 122 is operable to enclose liquid culture medium 10 between cell culture surface 116 and stabilizer device 120 thereby limiting the free range of motion of liquid culture medium 10 within cell culture chamber 104. Magnet 126 may be positioned adjacent bottom wall 108 to thereby pull magnet 126 toward bottom wall 108 thereby compressing substrate 122 against liquid culture medium 10. In this instance, liquid culture medium 10 is further stabilized by the compression of stabilizing device 120 toward cell culture surface 116 with liquid culture medium 10 positioned therebetween.

It should be understood that in other versions substrate 122 may include a flat sheet, a flat sheet with raised sides, at least one air pocket molded therein, etc. In other versions, substrate 122 may include a plurality of open areas 128 disposed along substrate 122 thereby providing fluid access through substrate 122. In this instance, substrate 122 may be molded as a solid grid pattern with the plurality of open areas 128 positioned along the surface of the grid such that a liquid medium, such as liquid culture medium 10 described above, may freely pass through substrate 122 via the plurality of open areas 128. It should be understood that substrate 122 of stabilizer device 120 may include various combinations of the features described above.

Figure 5:
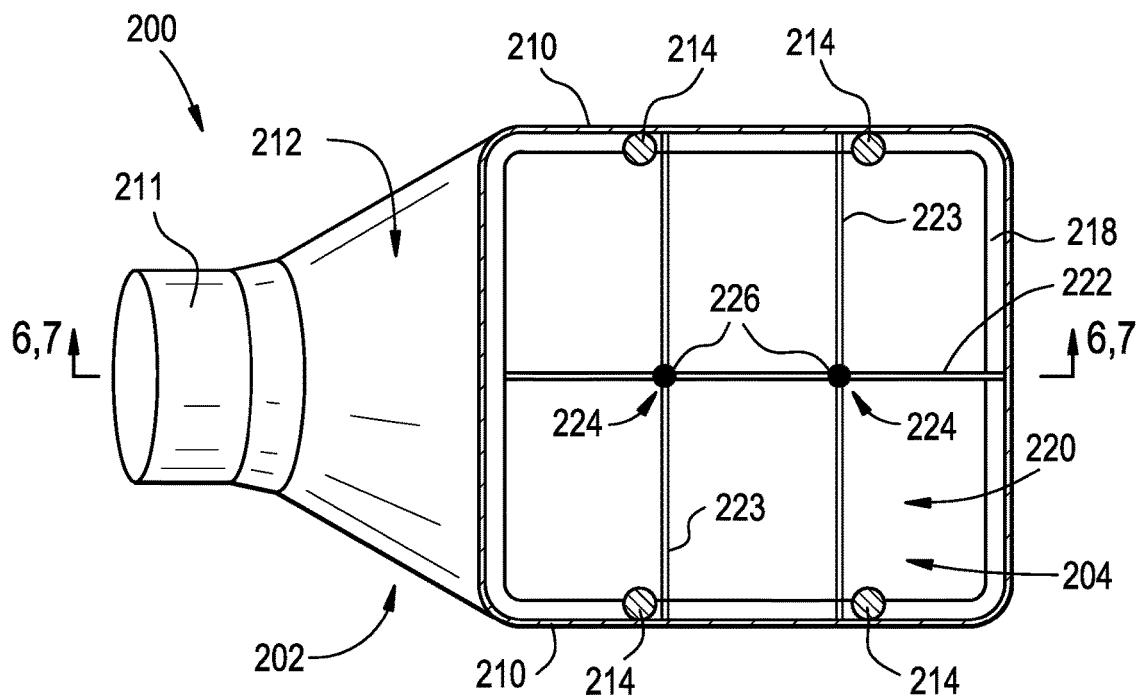
FIG. 5 depicts a top cross-sectional view of another cell culture vessel with a stabilizer grid, the cell culture vessel including a microcavity substrate and support columns therein, the stabilizer grid including at least one magnet integrally formed thereon according to one or more embodiments shown and described herein.
Figure 6:
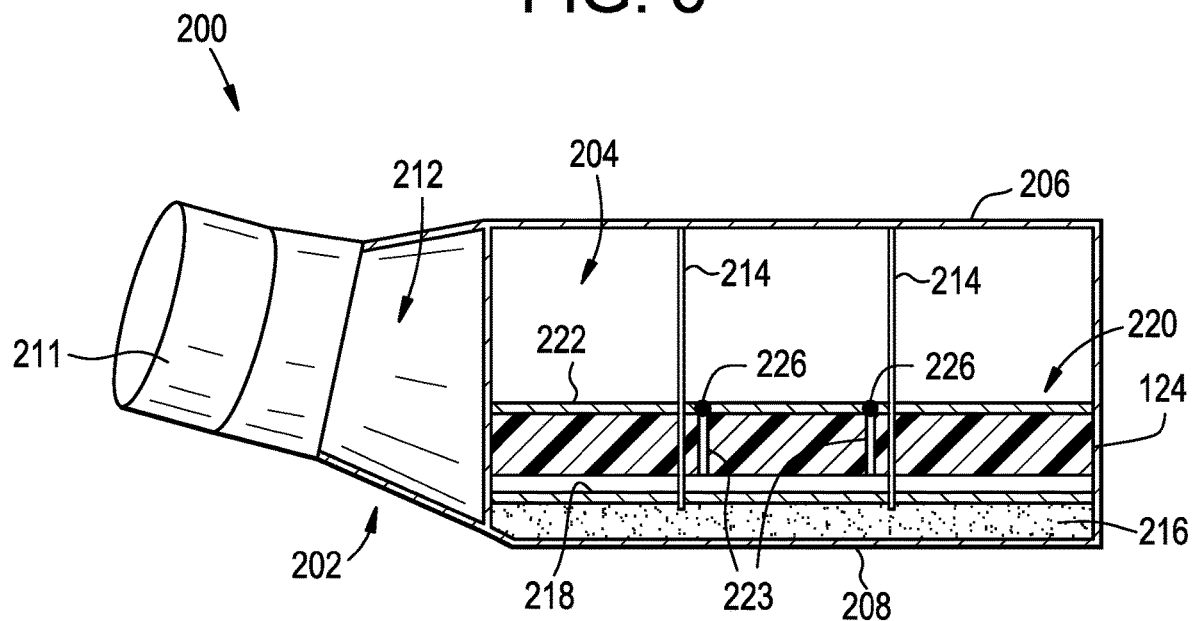
FIG. 6 depicts a side cross-sectional view of the cell culture vessel of FIG. 5 including a shelf positioned between the microcavity substrate and the stabilizer grid, the cross-section taken along line 6-6 of FIG. 5.

FIG. 5 and FIG. 6 show another version of a cell culture vessel 200 having a vessel body 202 that defines a cell culture chamber 204 formed within vessel body 202. Vessel body 202 comprises a top wall 206, a bottom wall 208, a plurality of sidewalls 210 and a plurality of support columns 214 extending therebetween. Vessel body 202 further includes an entry port 212 that is configured to provide fluid access into cell culture chamber 204 where a cell culture surface 216 and shelf 218 are positioned. Except as otherwise described below, it should be understood that vessel body 202, cell culture chamber 204, walls 206, 208, 210, entry port 212, support columns 214, cell culture surface 216 and shelf 218 may be configured and operable just like vessel body 102, cell culture chamber 104, walls 106, 108, 110, side entry port 112, support columns 114, cell culture surface 116 and shelf 118, respectively, described above. Thus, it should be understood that, in many respects, cell culture vessel 200 functions substantially similar to cell culture vessel 100 except for the differences explicitly noted herein.

For instance, cell culture vessel 200 includes a stabilizer device 220 positioned within cell culture chamber 204. Stabilizer device 220 comprises a plurality of interconnected grid segments 222, 223 forming a grid within cell culture chamber 204. In particular, stabilizer device 220 includes at least one first stabilizer wall 222 extending parallel to bottom wall 208 between opposing ends of cell culture chamber 204, and at least one second stabilizer wall 223 extending perpendicular to bottom wall 208 between opposing sidewalls 210 of cell culture chamber 204. Accordingly, first stabilizer wall 222 is perpendicular to second stabilizer wall 223 and intersects second stabilizer wall 223 at an intersection point 224, thereby forming interconnected grid segment 222, 223 that provide support for stabilizer device 220. In the present example, as seen in FIG. 5, stabilizer device 220 includes one first stabilizer wall 222 extending parallel to bottom wall 208 and two second stabilizer walls 223 extending perpendicular to bottom wall 208 thereby forming two intersection points 224 between each second stabilizer wall 223 and first stabilizer wall 222. It should be understood that stabilizer device 220 may include fewer or additional grid walls 222, 223 and intersection points 224 than that shown in the present example.

Support columns 214 extend adjacent to second stabilizer walls 223 such that support columns 214 are configured to abut against stabilizer device 220. In this instance, support columns 214 are operable to limit the range of motion of stabilizer device 220 within cell culture chamber 204. In particular, cell culture vessel 200 includes four support columns 214 positioned against second stabilizer walls 223 of stabilizer device 220 such that support columns 214 restrict stabilizer device 220 from moving laterally relative to top wall 206 and bottom wall 208. In other words, support columns 214 are configured to inhibit lateral movement of grid walls 222, 223 within cell culture chamber 204 and thereby solely permit vertical movement of grid walls 222, 223 along a length of support columns 214.

Stabilizer device 220 further includes at least one magnet 226 integrally formed within the plurality of grid walls 222, 223. In the present example, stabilizer device 220 includes two magnets 226 positioned along first stabilizer wall 222 at intersection points 224 of second stabilizer walls 223 and first stabilizer wall 222. It should be understood that stabilizer device 220 may include fewer or additional magnets 226 formed therein and/or may further include magnets 226 at various other positions along grid walls 222, 223. As best seen in FIG. 6, magnets 226 are positioned along stabilizer device 220 along a top end of first stabilizer wall 222. Grid walls 222, 223 include a predetermined length that terminates at a bottom end such that the bottom end of grid walls 222, 223 engage shelf 218 when in a lowered position.

Magnets 226, which comprise a predetermined polarization, facilitate movement of the plurality of grid walls 222, 223 within cell culture chamber 204 in response to placing an external magnet 228 adjacent vessel body 202. External magnet 228 comprises an opposite polarization as magnets 226 such that external magnet 228 and magnets 226 are magnetically attracted to one another. In other embodiments, magnets 226, 228 may have a same polarization such that magnets 226, 228 repel one another. Accordingly, as will be described in greater detail below, positioning external magnet 228 adjacent to vessel body 202 along top wall 206 or bottom wall 208 will cause magnets 226 to interact with external magnet 228 to thereby move the plurality of grid walls 222, 223 toward the respective wall 206, 208 that external magnet 228 is positioned adjacent to.

Figure 7A:
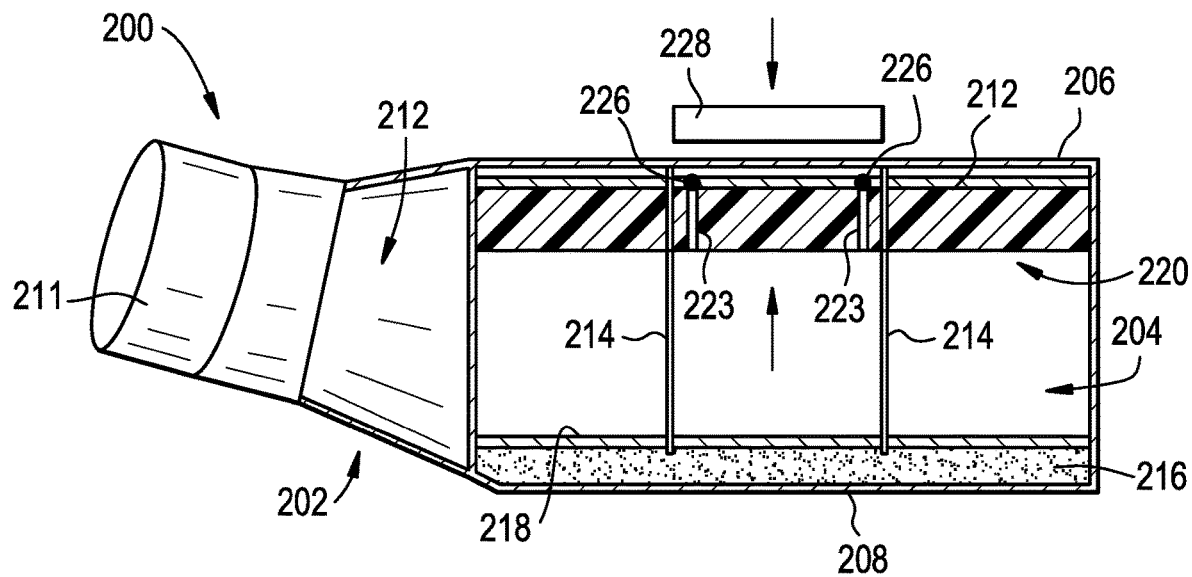
FIG. 7A depicts a side cross-sectional view of the cell culture vessel of FIG. 5 with an external magnet positioned over the vessel thereby translating the stabilizer grid toward the external magnet, the cross-section taken along line 7-7 of FIG. 5.
Figure 7B:
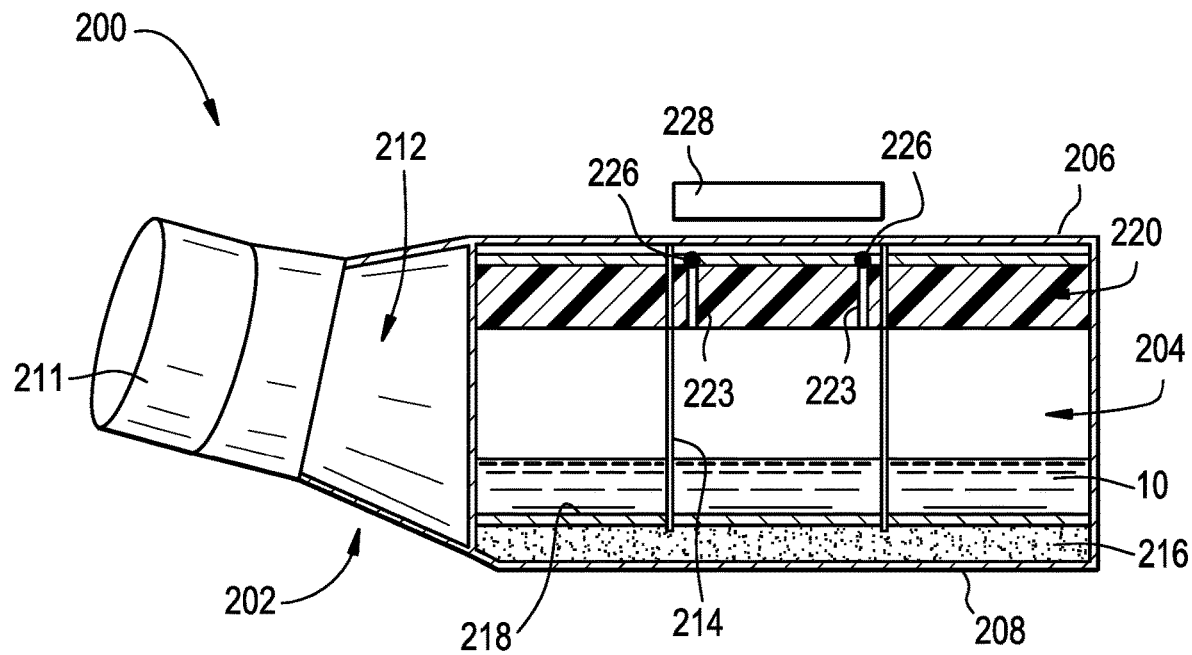
FIG. 7B depicts a side cross-sectional view of the cell culture vessel filled with a liquid medium while the stabilizer grid is held at a raised position proximate to the external magnet, the cross-section taken along line 7-7 of FIG. 5.

In use, as seen in FIG. 7A, stabilizer device 220 is raised within cell culture chamber 204 by positioning external magnet 228 against top wall 206 of vessel body 202. In this instance, the plurality of grid walls 222, 223 are lifted relative to cell culture surface 216 such that liquid culture medium 10 may subsequently be deposited directly onto cell culture surface 216 without encountering stabilizer device 220, as seen in FIG. 7B. Accordingly, with stabilizer device 220 raised toward top wall 206, the plurality of grid walls 222, 223 may not interfere with cell culture surface 216 receiving liquid control medium 10 thereon. At the conclusion of the liquid filling operation, stabilizer device 220 is lowered toward bottom wall 208 to thereby rest the plurality of grid walls 222, 223 over liquid culture medium 10. This may be achieved by one of several processes.

Figure 7C:
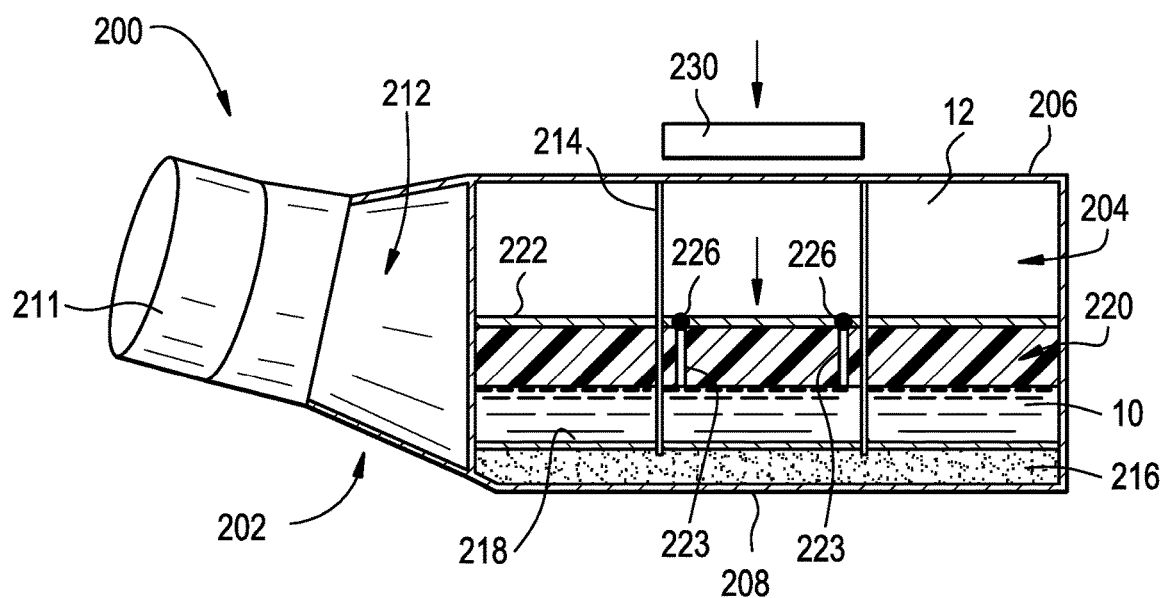
FIG. 7C depicts a side cross-sectional view of the cell culture vessel filled with the liquid medium and a second external magnet positioned over the vessel thereby translating the stabilizer grid away from the second external magnet, the cross-section taken along line 7-7 of FIG. 5.

As seen in FIG. 7C, a second external magnet 230, comprising a same polarization as magnets 226 of stabilizer device 220, is positioned against top wall 206. Accordingly, positioning second external magnet 230 adjacent to top wall 206 of vessel body 202 causes magnets 226 to interact with second external magnet 230 to thereby repel stabilizer device 220 away from top wall 206 due to the same polarization of magnets 226 and second external magnet 230. In this instance, the plurality of grid walls 222, 223 slidingly translate along the length of support columns 214 toward bottom wall 208 until encountering a top surface of liquid control medium 10. The placement of second external magnet 230 at top wall 206 may be maintained to thereby sustain a constant compressive force by stabilizer device 220 against liquid control medium 10 such that grid walls 222, 223 are operable to enclose liquid culture medium 10 between cell culture surface 216 and stabilizer device 220 for a preferred duration. The positioning of stabilizer device 220 against liquid control medium 10 serves to limit the free range of motion of liquid control medium 10 within cell culture chamber 204. Accordingly, stabilizer device 220 of the present example is configured to preserve the condition of the cells received within the microcavities of the cell culture surface 216 by inhibiting movement of liquid control medium 10 and isolating liquid control medium 10 from open volume areas 12 within cell culture chamber 204.

In other instances, external magnet 228 may simply be removed from top wall 206 to thereby terminate the magnetic interaction between magnets 226 and external magnet 228. In this instance the plurality of grid walls 222, 223 are no longer constrained to a raised position against top wall 206 and are thereby permitted to return to a lowered position by natural gravitational forces. With liquid control medium 10 now received over cell culture surface 216, stabilizer device 220 encounters a top surface of liquid control medium 10 thereby providing a planar surface of grid walls 222, 223 against liquid control medium 10 to minimize its fluidity within cell culture chamber 204.

In still other versions, external magnet 228 may be used to lower stabilizer device 220 within cell culture chamber 204. In this instance external magnet 228 is positioned adjacent bottom wall 208 to thereby attract magnets 226 toward bottom wall 208 since external magnet 228 comprises an opposite polarization as magnets 226. Accordingly, the plurality of grid walls 222, 223 are lowered by magnetic attraction and thereby compress against liquid culture medium 10 when encountering a top surface of liquid control medium 10. In this instance, liquid culture medium 10 is stabilized by the compression of stabilizer device 220 toward cell culture surface 216 with liquid culture medium 10 positioned therebetween.

Figure 8:
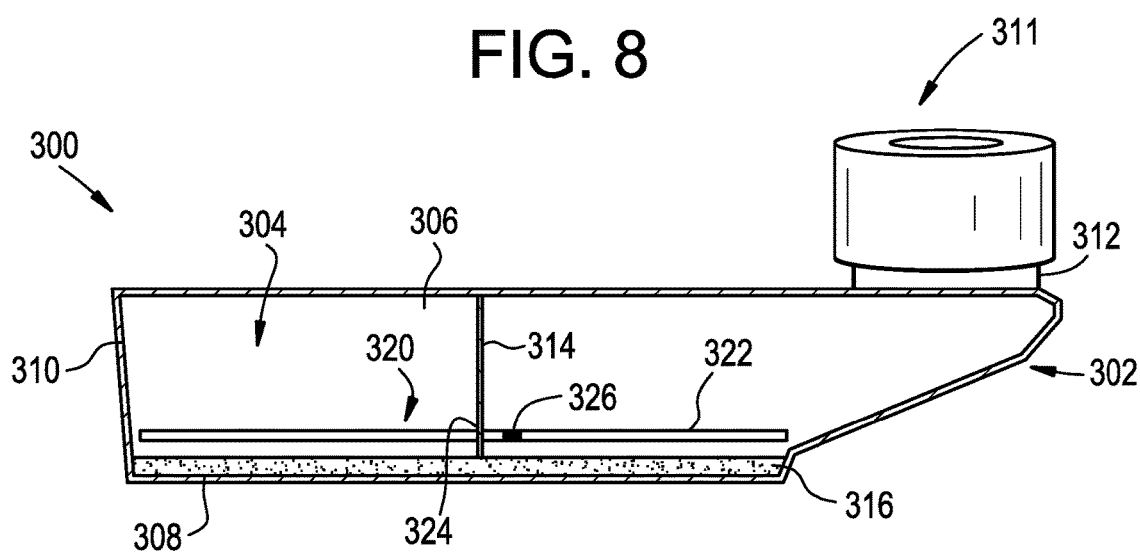
FIG. 8 depicts a side cross-sectional view of an another cell culture vessel with a stabilizer device, the cell culture vessel having a low profile body and support columns therein, the stabilizer device having a magnet formed therein according to one or more embodiments shown and described herein.

FIG. 8 shows a cell culture vessel 300 that is substantially similar to cell culture vessel 100, and therefore like reference numerals are used to identify like components. However, cell culture vessel 300 is different than cell culture vessel 100 in that cell culture vessel 300 has a low profile body 302 that allows cell culture chamber 304 of cell culture vessel 300 to be completely filled with liquid control medium 10 due to the relative position of cap 311 on top wall 306. In particular, sidewalls 310 of body 302 may comprise a vertical height of approximately 0.5 centimeters to approximately 1.0 centimeters; however, it should be understood that sidewalls 310 of cell culture vessel 300 may include other dimensions. Due to the low profile of cell culture vessel 300, cap 311 is positioned along top wall 306 of body 302, rather than along a sidewall 310 of body 302 as included on cell culture vessels 100, 200 described above. Cell culture vessel 300 does not include a shelf within cell culture chamber 304; however, in other versions cell culture chamber 304 may include a shelf positioned adjacent to cell culture surface 316.

Cell culture vessel 300 includes a stabilizer device 320 that is configured and operable similar to stabilizer device 120 described above, except for the differences explicitly noted herein. Stabilizer device 320 comprises a substrate 322 that includes a magnet 326 integrally formed therein. Substrate 322 further includes a plurality of slots 324 that are sized and shaped to slidably receive a plurality of support columns 314 of body 302 therethrough. As similarly described in detail above with respect to cell culture vessel 100, support columns 314 of cell culture vessel 300 are configured to guide stabilizer device 320 between top wall 306 and bottom wall 308 along a length of support columns 314. Accordingly, support columns 314 are configured to inhibit the lateral movement of stabilizer device 320 within cell culture chamber 304.

Figure 9A:
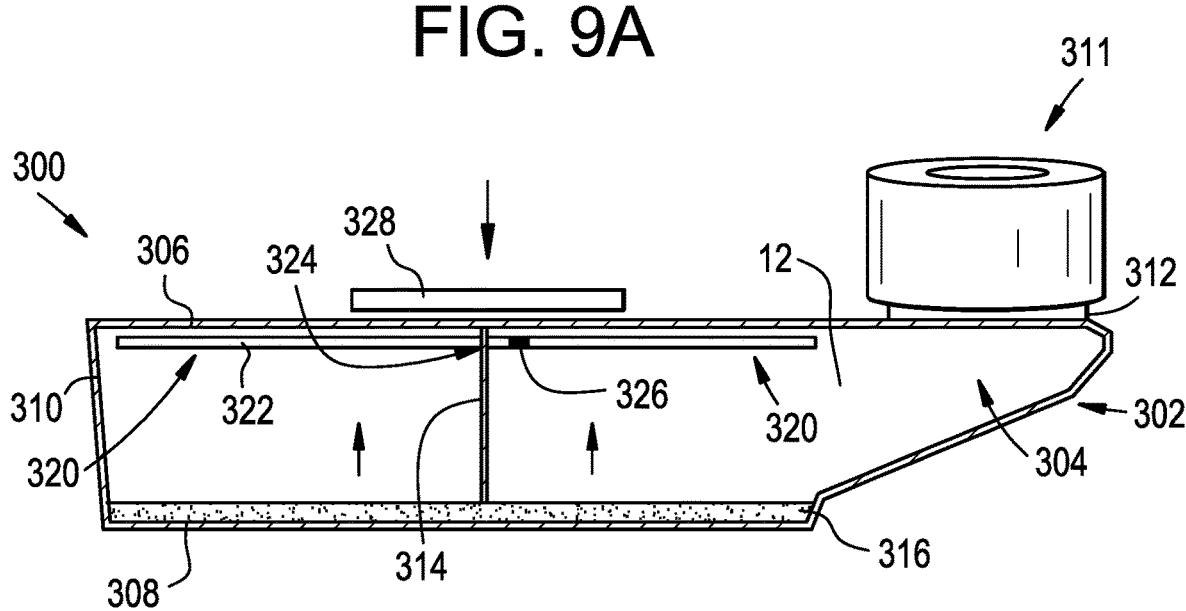
FIG. 9A depicts a side cross-sectional view of the cell culture vessel of FIG. 8 with an external magnet positioned over the vessel thereby translating the stabilizer device toward the external magnet.
Figure 9B:
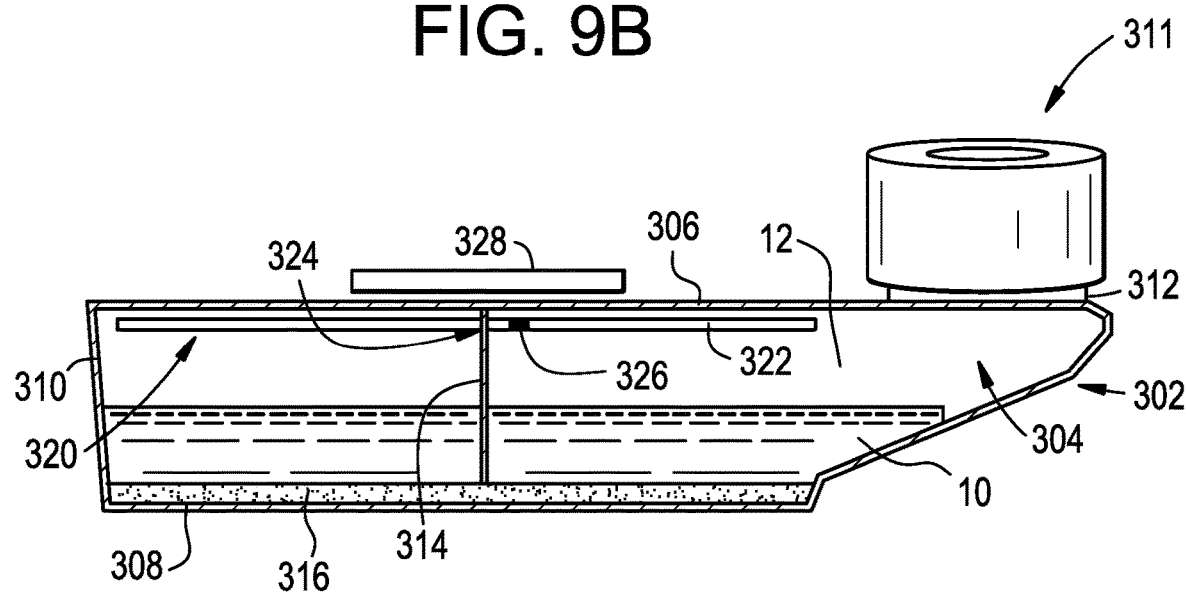
FIG. 9B depicts a side cross-sectional view of the cell culture vessel filled with a liquid medium while the stabilizer device is held at a raised positioned proximate to the external magnet.

During use of cell culture vessel 300, an external magnet 328 is positioned along top wall 306 of body 302 thereby attracting magnet 326 of substrate 322 relatively upward toward top wall 306, as seen in FIG. 9A. In this instance, magnet 326 and external magnet 328 comprise opposite magnetic polarizations such that magnet 326 is magnetically attracted to external magnet 328, thereby causing substrate 322 to slidably translate along support columns 314 toward top wall 306. With substrate 322 located at a raised position within cell culture chamber 304, liquid culture medium 10 is then inserted into cell culture vessel 300 via entry port 312 such that liquid culture medium 10 is deposited directly onto cell culture surface 316, as seen in FIG. 9B. To stabilize liquid control medium 10, external magnet 328 is removed from top wall 306 thereby terminating the magnetic attraction of magnet 326 toward top wall 306. Accordingly, substrate 322 lowers within cell culture chamber 304, due to natural gravitational forces, until encountering a top surface of liquid culture medium 10.

Figure 9C:
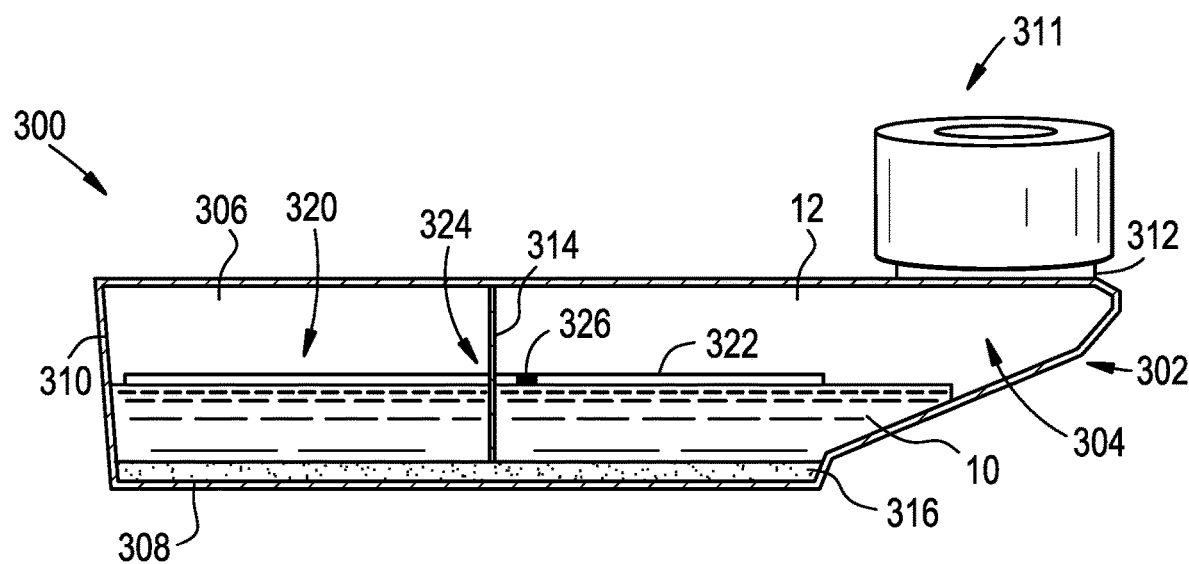
FIG. 9C depicts a side cross-sectional view of the cell culture vessel with the liquid medium deposited over the microcavity substrate and the external magnet removed thereby causing the stabilizer device to return toward the microcavity substrate and float along a surface of the liquid medium.

FIG. 9C shows substrate 322 positioned over liquid culture medium 10 such that stabilizer device 320 is operable to stabilize the fluidity of liquid culture medium 10 within cell culture chamber 304, thereby ensuring liquid culture medium 10 is deposited over cell culture surface 316 without experiencing excessive turbulence or movement. Accordingly, stabilizer device 320 is configured to preserve the condition of the cells received within the microcavities of the cell culture surface 316 by inhibiting movement of liquid control medium 10 and isolating liquid control medium 10 from open volume areas 12 within cell culture chamber 304. In other words, separating liquid control volume 10 from open volume areas 12 of cell culture chamber 304 minimizes the ability of liquid control volume 10 to have adequate space to move therein as cell culture vessel 300 is physically transported.

Figure 10:
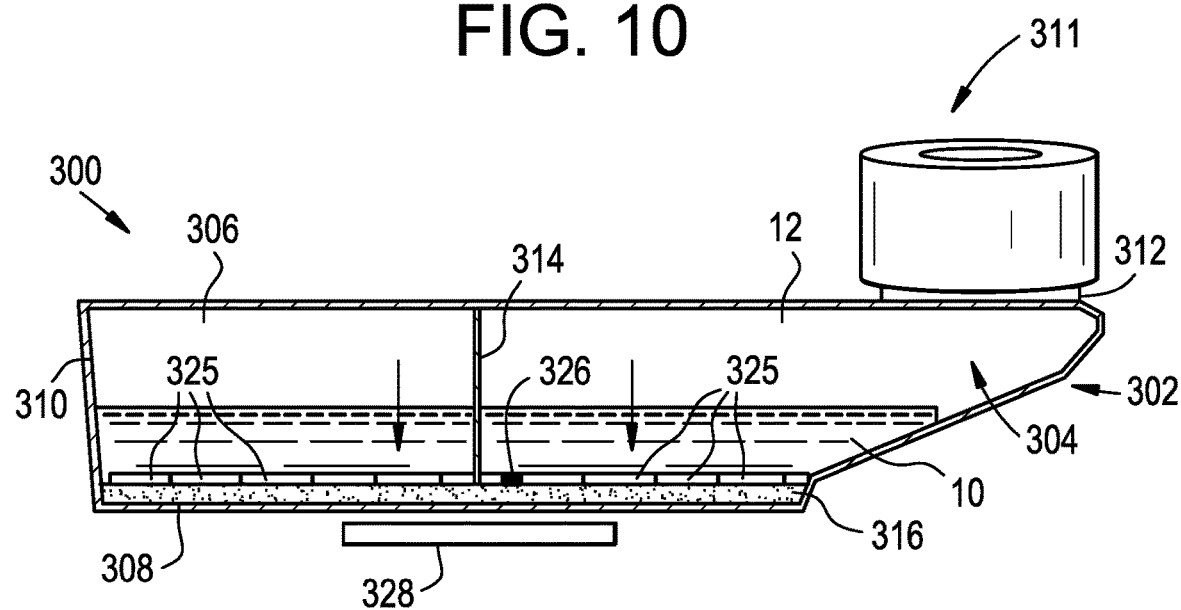
FIG. 10 depicts a side cross-sectional view of another stabilizer device, the stabilizer device having a porous substrate and a magnet formed therein, the cell culture vessel having a liquid medium deposited over a microcavity substrate and an external magnet positioned under the vessel thereby lowering the stabilizer device underneath the liquid medium and against the microcavity substrate according to one or more embodiments shown and described herein.

In other versions, as seen in FIG. 10, stabilizer device 320 may have a porous structure such that substrate 322 includes a plurality of pores 325 disposed along a length of substrate 322. In this instance, substrate 322 is configured to translate through liquid control medium 10 after cell culture chamber 304 receives liquid control medium 10 along cell culture surface 316. In particular, to stabilize liquid control medium 10, external magnet 328 is removed from top wall 306 and repositioned adjacent to bottom wall 308 to thereby magnetically draw magnet 326 of substrate 322 toward bottom wall 308. Upon initially encountering a top surface of liquid control medium 10, substrate 322 continues to slidably translate along the length of the plurality of support columns 314 and toward bottom wall 308 due to the presence of the plurality of pores 325 along substrate 322. In other words, substrate 322 is capable of passing through liquid control medium 10 by redirecting liquid control medium 10 through the plurality of pores 325 of substrate 322 as substrate 322 translates along support columns 314 and toward cell culture surface 316.

In this instance, as best seen in FIG. 10, stabilizer device 320 is ultimately positioned against cell culture surface 316 and proximate to bottom wall 308 such that liquid control medium 10 is repositioned atop substrate 322. With substrate 322 located along cell culture surface 316 and along a bottom surface of liquid control medium 10, rather than a top surface of liquid control medium 10 as previously described above, stabilizer device 320 of the present example is configured to preserve the condition of the cells received within the microcavities of the cell culture surface 316 by substantially isolating the microcavity substrate from liquid control medium 10. Accordingly, despite liquid control medium 10 having ability to move within cell culture chamber 304 due to the ample open volume area 12 therein, stabilizer device 320 separates cell culture surface 316 from liquid control medium 10 thereby stabilizing the cells received within cell culture surface 316.

Alternatively, in other instances, external magnet 328 may be positioned adjacent bottom wall 308 prior to filling cell culture vessel 300 with liquid culture medium 10 such that stabilizer device 320 is positioned against cell culture surface 316. In this instance, cells may be deposited into the microcavities of cell culture surface 316 through the plurality of pores 325 of substrate 322. Accordingly, in the present example the plurality of pores 325 are sized and shaped to receive cells therethrough to thereby facilitate the seeding of cells into the microcavity substrate of cell culture surface 316 despite substrate 322 being positioned thereon. In this instance, substrate 322 is already in a lowered position, securing the cells of cell culture surface 316 prior to cell culture vessel 300 receiving liquid control medium 10 within cell culture chamber 304.

Figure 11:
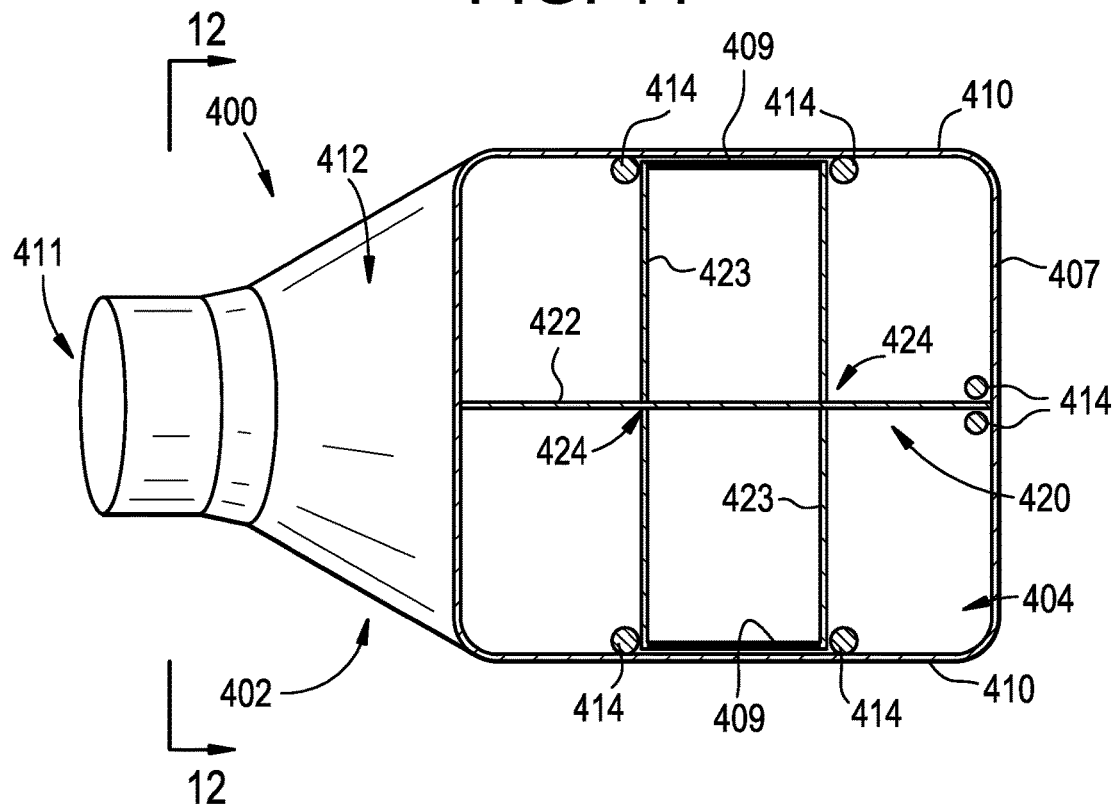
FIG. 11 depicts a top cross-sectional view of another cell culture vessel with a stabilizer device, the cell culture vessel including a support columns and a pair of pivot bars, the stabilizer device being pivotably coupled to the pivot bars according to one or more embodiments shown and described herein.

FIG. 11 shows an another embodiment of a cell culture vessel 400 that is substantially similar to cell culture vessel 100, and therefore like reference numerals are used to identify like components. However, cell culture vessel 400 is different than cell culture vessel 100 in that cell culture vessel 400 includes at least two pivot bars 409 extending along sidewalls 410 of body 402. In particular pivot bars 409 extend parallel to bottom wall 408 and each pivot bar 409 is positioned between a pair of support columns 414 of a plurality of support columns 414. In the present example, body 402 includes six support columns 414 with a first pair of support columns 414 positioned along a first sidewall 410 and a second pair of support columns 414 positioned along a second, opposite sidewall 410. As further seen in FIG. 11, a third pair of support columns 414 is positioned along a back wall 407 of body 402. Back wall 407 is positioned opposite of entry port 412 and defines a distal end of cell culture chamber 404 extending between the pair of sidewalls 410.

Cell culture vessel 400 includes a stabilizer device 420 within cell culture chamber 404. Stabilizer device 420 comprises a plurality of grid walls 422, 423 (i.e. wings) that collectively form a grid. In particular, stabilizer device 420 comprises at least one first stabilizer wall 422 (i.e. central wing) extending parallel to bottom wall 408 and at least one second stabilizer wall 423 (i.e. outboard wing) extending perpendicular to bottom wall 408 such that first stabilizer wall 422 is perpendicular to second stabilizer wall 423. In the present example, stabilizer device 420 includes one first stabilizer wall 422 and two second stabilizer walls 423. First stabilizer wall 422 of stabilizer device 420 is slidingly coupled to the pair of support columns 414 positioned along back wall 407. As will be described in greater detail below, first stabilizer wall 422 is configured to translate within cell culture chamber 404 along the lengths of support columns 414.

Each second stabilizer wall 423 is pivotably coupled to first stabilizer wall 422 at an intersection point 424, as seen in FIG. 11, such that second stabilizer walls 423 are configured to pivot relative to first stabilizer wall 422. First stabilizer wall 422 is positioned between the pair of second stabilizer walls 423. Second stabilizer walls 423 are further pivotably coupled to body 402 at sidewalls 410. In particular, sidewalls 410 each include a pivot bar 409 extending thereon such that second stabilizer walls 423 are configured to couple to pivot bars 409 and pivot within cell culture chamber 404 about pivot bars 409. It should be understood that stabilizer device 420 may include fewer or additional grid walls 422, 423 and intersection points 424 than that shown.

Figure 12A:
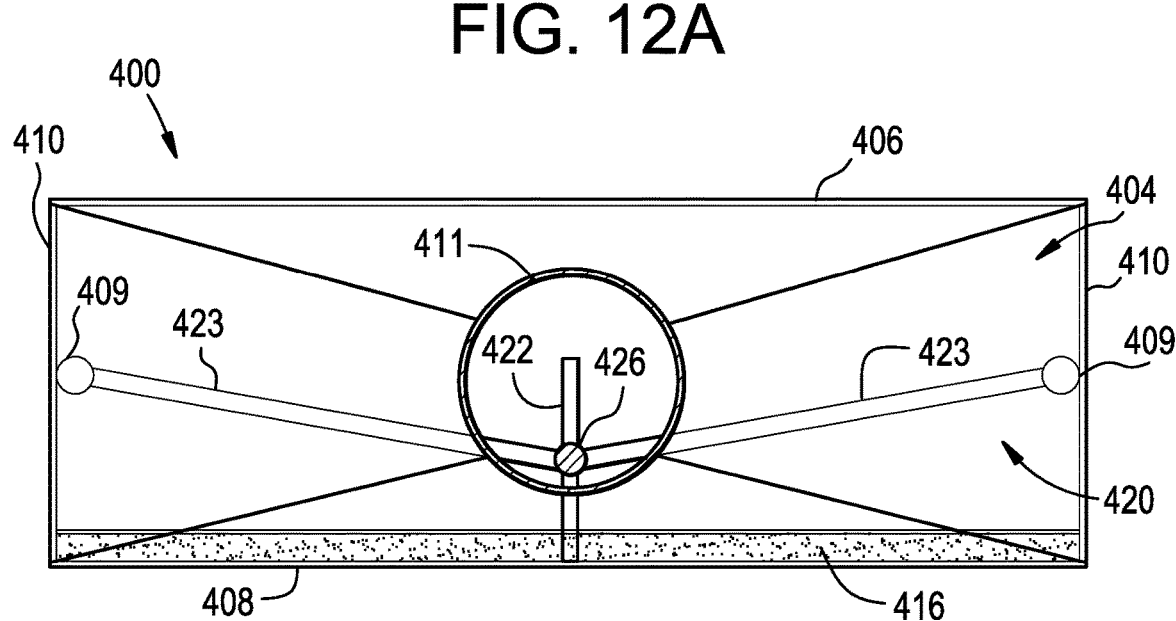
FIG. 12A depicts a front cross-sectional view of the cell culture vessel of FIG. 11 with the stabilizer device positioned in a lowered positioned about the pivot bars, the cross-section taken along line 12-12 of FIG. 11.
Figure 12B:
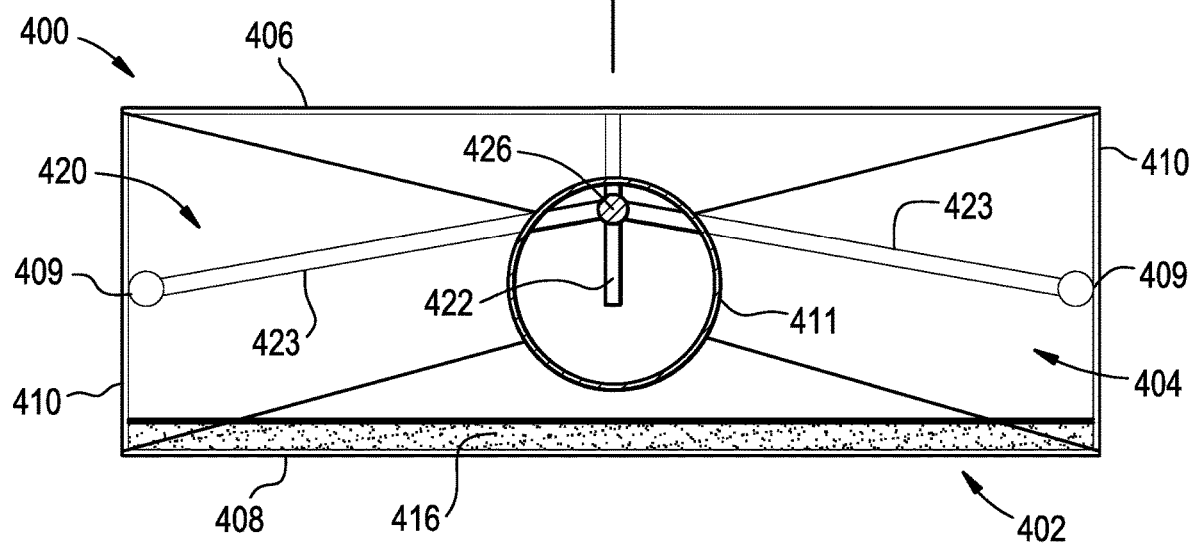
FIG. 12B depicts a front cross-sectional view of the cell culture vessel of FIG. 11 with the stabilizer device positioned in a raised positioned about the pivot bars, the cross-section taken along line 12-12 of FIG. 11.

During use of cell culture vessel 400, stabilizer device 420 is initially in a lowered position such that first stabilizer wall 422 is positioned adjacent to bottom wall 408 of body 402, as seen in FIG. 12A. In this instance, second stabilizer walls 423 are pivoted downward relative to pivot bars 409 to facilitate the lowered orientation of first stabilizer wall 422. Stabilizer device 420 is raised within body 402 through use of a graspable instrument. In particular, the instrument is inserted into a connector 426 of stabilizer device 420 to thereby pivot stabilizer device 420 relative to cell culture chamber 404. In the present example, connector 426 is positioned along first stabilizer wall 422 adjacent to entry port 412 such that connector 426 is easily accessible to a user once cap 411 of cell culture vessel 400 is opened. With connector 426 exposed through entry port 412, a user manually manipulates stabilizer device 420 by inserting the instrument into connector 426 and subsequently rising first stabilizer wall 422 toward top wall 406. As seen in FIG. 12B, raising first stabilizer wall 422 toward top wall 406 causes second stabilizer walls 423 to pivot relative to both pivot bars 409 and first stabilizer wall 422 at intersection points 424. It should be understood that the instrument may comprise a stripette, pipet, or other various suitable instruments.

Figure 13:
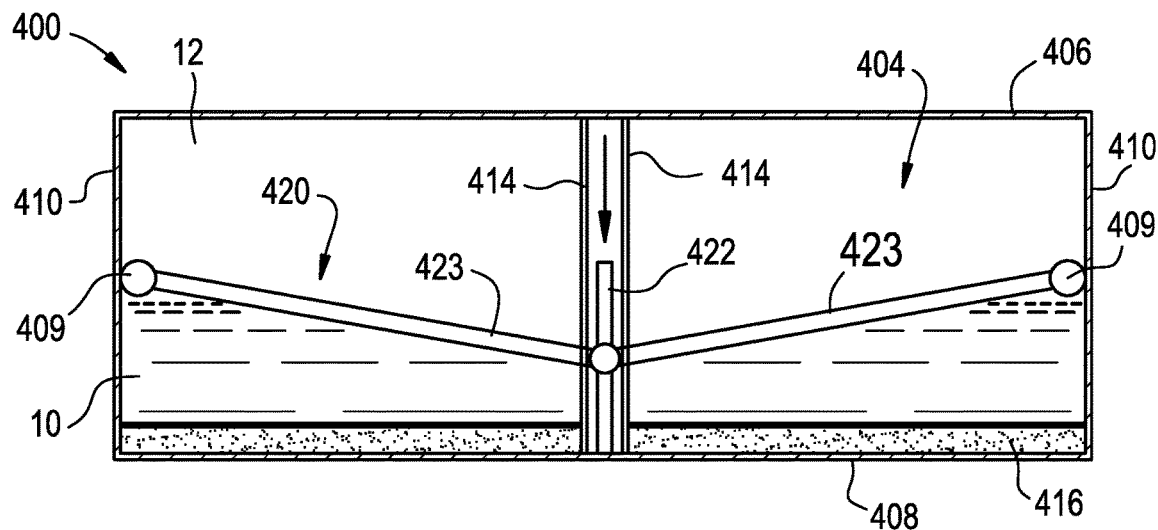
FIG. 13 depicts a rear cross-sectional view of the cell culture vessel of FIG. 11 with the stabilizer device positioned in a lowered positioned about the pivot bars with a liquid medium received underneath, the cross-section taken along line 13-13 of FIG. 11.

With stabilizer device 420 in a raised position distal from bottom wall 408, liquid control medium 10 is inserted into cell culture chamber 404 and deposited over cell culture surface 416 without encountering interference from stabilizer device 420. Once cell culture vessel 400 has received ample liquid control medium 10 therein, stabilizer device 420 is lowered toward bottom wall 408 to thereby compress liquid control medium 10 against the plurality of grid walls 422, 423. In particular, as seen in FIG. 13, first stabilizer wall 422 is slidably translated between the pair of support columns 414 along back wall 407 by reinserting the instrument into connector 426. With first stabilizer wall 422 of stabilizer device 420 received between support columns 414 along back wall 407, stabilizer device 420 is restricted to translating along the length of support columns 414 thereby effectively limiting lateral movement of stabilizer device 420. Accordingly, the range of motion that second stabilizer walls 423 are capable of pivoting about pivot bars 409 is limited.

In this instance, the plurality of grid walls 422, 423 are positioned directly over liquid culture medium 10 such that stabilizer device 420 is operable to stabilize the fluidity of liquid culture medium 10 within cell culture chamber 404, thereby ensuring liquid culture medium 10 is deposited over cell culture surface 416 without experiencing excessive turbulence or movement when cell culture vessel 400 is moved. Accordingly, stabilizer device 420 is configured to preserve the condition of the cells received within the microcavities of the cell culture surface 416 by inhibiting movement of liquid control medium 10 and isolating liquid control medium 10 from open volume areas 12 within cell culture chamber 404. In other words, separating liquid control volume 10 from open volume areas 12 of cell culture chamber 404 minimizes the ability of liquid control volume 10 to have adequate space to move therein as cell culture vessel 400 is physically transported.

The above-described cell culture vessels include various stabilizer devices positioned within the respective cell culture chambers of the vessel. The stabilizer devices described herein are capable of being repositioned and/or moved within the cell culture chamber to facilitate both the receipt of a liquid medium along the cell culture surface of the vessel and the stabilization of the liquid medium relative to the cell culture surface. The stabilizer devices described herein include structural support features for inhibiting free motion and/or fluidity of the liquid medium and/or other fluids contained within the vessel, the structural support features being capable of manual actuation by magnetic levitation and/or other various methods as described in detail above. Based on the foregoing, it should be understood that the stabilizer devices described herein may be used to stabilize a liquid medium contained within the cell culture vessel when physically maneuvering and/or transporting the vessel, thereby minimizing the amount of movement of the liquid medium within the vessel and reducing the potential for turbulence against the cells being cultured along the cell culture surface of the vessel.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A cell culture vessel, comprising:
 a vessel body that defines a cell culture chamber enclosed between a bottom wall and a top wall;
 a support column within the cell culture chamber extending between the top wall and the bottom wall;
 a stabilizer device covering a width and length of the cell culture chamber having a column engaging structure that is sized to slidingly engage the support column such that the stabilizer device is movable along the support column as a liquid culture medium is received in the cell culture chamber;
 wherein the support column guides the stabilizer device along a length of the support column as the stabilizer device rises with rising liquid level in the cell culture chamber during a liquid culture medium filling operation; and
 wherein the vessel body includes a shelf that extends into the cell culture chamber and a cell culture surface positioned within the cell culture chamber, the shelf located above the cell culture chamber to engage the stabilizer device and inhibit movement of the stabilizer device toward the cell culture surface.

2. The cell culture vessel of claim 1, wherein a cell culture surface is located along the bottom wall and defines a cell culturing area, the stabilizer device having a footprint on the cell culture surface that is at least 50 percent of the cell culturing area.

3. The cell culture vessel of claim 2, wherein the stabilizer device comprises a material having a density no greater than about 1.0 g/cm$^3$ at room temperature such that the stabilizer device floats at a surface of a liquid culture medium received in the cell culture chamber.

4. The cell culture vessel of claim 3 wherein the stabilizer device is in the form of a substrate comprising a polymer.

5. The cell culture vessel of claim 1, wherein the stabilizer device comprises a magnet disposed therein such that the magnet is integral with the stabilizer device.

6. The cell culture vessel of claim 5, further comprising an external magnet positioned against the top wall or the bottom wall, wherein the external magnet has a polarization the same as or opposite than the polarization of the magnet disposed within the stabilizer device thereby interacting with the magnet disposed within the stabilizer device.

7. The cell culture vessel of claim 1, wherein the cell culture surface comprises a microcavity substrate that defines a plurality of microcavities sized and configured to receive cells therein.

8. The cell culture vessel of claim 1, wherein the stabilizer device includes an air pocket integrally formed within the stabilizer device.

9. The cell culture vessel of claim 1, wherein the stabilizer device comprises a grid comprising a plurality of interconnected grid segments, a first stabilizer wall that extends between opposite ends of the grid and a second stabilizer wall that extends between opposite sides of the grid, wherein the first stabilizer wall is perpendicular to the second stabilizer wall.

10. The cell culture vessel of claim 9, wherein the grid includes at least one magnet carried by at least one of the first and second stabilizer walls.

11. The cell culture vessel of claim 10, further comprising an external magnet positioned against the top wall or the bottom wall, wherein the external magnet has a polarization the same or opposite than the magnet disposed within the grid thereby interacting with the magnet disposed within the grid.

12. The cell culture vessel of claim 9, wherein the grid is pivotally coupled to the vessel body such that the first and second stabilizer walls pivot relative to the bottom wall.

13. The cell culture vessel of claim 12, wherein the grid comprises a connector that receives a pipet or stripette to manually pivot the grid relative to the cell culture chamber.

14. The cell culture vessel of claim 1, wherein the stabilizer device comprises a porous substrate that includes a plurality of pores formed therein.

15. The cell culture vessel of claim 14, wherein the porous substrate includes a magnet integrally formed therein, wherein the cell culture vessel comprises an external magnet positioned against the top wall or the bottom wall, wherein the external magnet has a polarization with the same or opposite than the polarization of the magnet disposed within the porous substrate thereby interacting with the magnet disposed within the porous substrate.

16. A cell culture vessel, comprising:
a vessel body that defines a cell culture chamber enclosed between a bottom wall and a top wall;
a support column within the cell culture chamber extending between the top wall and the bottom wall;
a stabilizer device covering a width and length of the cell culture chamber having a column engaging structure that is sized to slidingly engage the support column such that the stabilizer device is movable along the support column as a liquid culture medium is received in the cell culture chamber;
wherein the support column guides the stabilizer device along a length of the support column as the stabilizer device rises with rising liquid level in the cell culture chamber during a liquid culture medium filling operation; and
wherein the stabilizer device comprises a grid comprising a plurality of interconnected grid segments, a first stabilizer wall that extends between opposite ends of the grid and a second stabilizer wall that extends between opposite sides of the grid, wherein the first stabilizer wall is perpendicular to the second stabilizer wall.

17. The cell culture vessel of claim 16, wherein the grid includes at least one magnet carried by at least one of the first and second stabilizer walls.

18. The cell culture vessel of claim 17, further comprising an external magnet positioned against the top wall or the bottom wall, wherein the external magnet has a polarization the same or opposite than the magnet disposed within the grid thereby interacting with the magnet disposed within the grid.

19. The cell culture vessel of claim 16, wherein the grid is pivotally coupled to the vessel body such that the first and second stabilizer walls pivot relative to the bottom wall.

20. The cell culture vessel of claim 19, wherein the grid comprises a connector that receives a pipet or stripette to manually pivot the grid relative to the cell culture chamber.

21. The cell culture vessel of claim 16, wherein the stabilizer device comprises a porous substrate that includes a plurality of pores formed therein.

22. The cell culture vessel of claim 21, wherein the porous substrate includes a magnet integrally formed therein, wherein the cell culture vessel comprises an external magnet positioned against the top wall or the bottom wall, wherein the external magnet has a polarization with the same or opposite than the polarization of the magnet disposed within the porous substrate thereby interacting with the magnet disposed within the porous substrate.

23. The cell culture vessel of claim 16, wherein a cell culture surface is located along the bottom wall and defines a cell culturing area, the stabilizer device having a footprint on the cell culture surface that is at least 50 percent of the cell culturing area.

24. The cell culture vessel of claim 23, wherein the stabilizer device comprises a material having a density no greater than about 1.0 g/cm$^3$ at room temperature such that the stabilizer device floats at a surface of a liquid culture medium received in the cell culture chamber.

25. The cell culture vessel of claim 24, wherein the stabilizer device is in the form of a substrate comprising a polymer.

26. The cell culture vessel of claim 16, wherein the stabilizer device comprises a magnet disposed therein such that the magnet is integral with the stabilizer device.

27. The cell culture vessel of claim 26, further comprising an external magnet positioned against the top wall or the bottom wall, wherein the external magnet has a polarization the same as or opposite than the polarization of the magnet disposed within the stabilizer device thereby interacting with the magnet disposed within the stabilizer device.

28. The cell culture vessel of claim 16, wherein the cell culture surface comprises a microcavity substrate that defines a plurality of microcavities sized and configured to receive cells therein.

29. The cell culture vessel of claim 16, wherein the stabilizer device includes an air pocket integrally formed within the stabilizer device.

\* \* \* \* \*